US011306066B2

(12) United States Patent
Chai et al.

(10) Patent No.: US 11,306,066 B2
(45) Date of Patent: *Apr. 19, 2022

(54) 4H-PYRAN COMPOUNDS AS INSULIN-REGULATED AMINOPEPTIDASE (IRAP) INHIBITORS

(71) Applicants: Monash University, Clayton (AU); The Florey Institute of Neuroscience and Mental Health, Melbourne (AU); St. Vincent's Institute of Medical Research, Fitzroy (AU)

(72) Inventors: Siew Yeen Chai, Clayton (AU); Philip Thompson, Parkville (AU); Simon Mountford, Parkville (AU); Michael W. Parker, Fitzroy (AU)

(73) Assignee: Monash University, Victoria (AU)

( * ) Notice: Subject to any disclaimer, the term of this patent is extended or adjusted under 35 U.S.C. 154(b) by 22 days.

This patent is subject to a terminal disclaimer.

(21) Appl. No.: 15/572,554

(22) PCT Filed: May 6, 2016

(86) PCT No.: PCT/AU2016/050332
§ 371 (c)(1),
(2) Date: Nov. 8, 2017

(87) PCT Pub. No.: WO2016/179645
PCT Pub. Date: Nov. 17, 2016

(65) Prior Publication Data
US 2018/0170891 A1 Jun. 21, 2018

(30) Foreign Application Priority Data
May 8, 2015 (AU) ................. 2015901676

(51) Int. Cl.
*A61K 31/351* (2006.01)
*A61K 31/352* (2006.01)
*A61K 31/35* (2006.01)
*C07D 309/32* (2006.01)
*C07D 311/74* (2006.01)
*C07D 311/02* (2006.01)
*C07D 311/00* (2006.01)
*A61P 25/28* (2006.01)
*C07D 405/04* (2006.01)
*C07D 405/10* (2006.01)
*C07D 493/04* (2006.01)
*C07D 407/10* (2006.01)
*C07D 409/10* (2006.01)

(52) U.S. Cl.
CPC ............ *C07D 309/32* (2013.01); *A61P 25/28* (2018.01); *C07D 405/04* (2013.01); *C07D 405/10* (2013.01); *C07D 407/10* (2013.01); *C07D 409/10* (2013.01); *C07D 493/04* (2013.01)

(58) Field of Classification Search
CPC .... A61K 31/351; A61K 31/352; A61K 31/35; C07D 309/32; C07D 311/74; C07D 311/02; C07D 311/00; A61P 25/28
USPC ........ 514/451, 456, 459; 549/356, 404, 405, 549/407, 396, 424, 425, 426, 427
See application file for complete search history.

(56) References Cited

U.S. PATENT DOCUMENTS

| 5,719,181 A | 2/1998 | Urbahns et al. |
| 5,874,462 A | 2/1999 | Urbahns et al. |
| 10,100,311 B2 * | 10/2018 | Chai ................. A61K 31/55 |
| 10,787,668 B2 * | 9/2020 | Chai ................. A61K 31/4709 |
| 2009/0181986 A1 * | 7/2009 | Abelman ............ C07D 211/90 514/259.3 |
| 2020/0362354 A1 * | 11/2020 | Chai ................. A61K 31/55 |

FOREIGN PATENT DOCUMENTS

WO WO 2009/065169 A1 5/2009

OTHER PUBLICATIONS

Pratap, U., D. Jawale, P. Netankarand R. Mane, "Baker's yeast catalyzed one-pot three-component synthesis of polyfunctionalized 4H-pyrans", Tetrahed. Lett. (2011), 52: pp. 5817-5819. (Year: 2011).*
STN Registry database entry: CAS RN 1215394-93-6. (Year: 2010).*
STN Registry database entry: CAS RN 902359-49-3. (Year: 2006).*
Marchalin, S., D. Ilavsky, J. Kovac and M. Bruncko, "Synthesis and reactions of 5-acetyl-2-amino-3-cyano-4-(5-X-2-Furyl)-6-methyl-4H-pyrans", Collect. Czech. Chem. Commun. (1990), 55: pp. 718-727. (Year: 1990).*
National Center for Biotechnology Information. "PubChem Compound Summary for CID 2839319" PubChem, https://pubchem.ncbi.nlm.nih.gov/compound/2839319. Accessed Jan. 13, 2021. (Year: 2005).*
National Center for Biotechnology Information. "PubChem Bioassay Record for AID 775, Screen for Chemicals that Extend Yeast Lifespan, Source: SRMLSC" PubChem, https://pubchem.ncbi.nlm.nih.gov/bioassay/775. Accessed Jan. 13, 2021. (Year: 2007).*
Rowe, R., P. Sheskey and M. Quinn, Handbook of Pharmaceutical Excipients, London: Pharmaceutical Press (2009). (Year: 2009).*
Ameen et al., Chinese Chemical Letters, 25 (2), 2013, pp. 212-214.
Amirnejad et al, Monatshefte für Chemie,144 (8),2013, pp. 1219-1225.
Database Registry, Chemical Abstracts Service, (Apr. 24, 2001), Database accession No. 3321 08-86-8.

(Continued)

Primary Examiner — Joseph R Kosack
Assistant Examiner — Sagar Patel
(74) Attorney, Agent, or Firm — Adsero IP

(57) ABSTRACT

The present disclosure relates generally, but not exclusively, to compounds and their use in therapy, to compositions and agents comprising said compounds, to methods of treatment using said compounds, and their use in the manufacture of medicaments. The disclosure further relates to inhibitors of IRAP and their use in the treatment or prevention of Alzheimer's disease and the treatment and prevention of memory and cognitive disorders.

25 Claims, 2 Drawing Sheets

(56) References Cited

OTHER PUBLICATIONS

Kalla et al., Tetrahedron Letters, 56 (5), 2015 (published online Dec. 19, 2014), pp. 717-720.
Kiyani et al., Research of Chemical Intermediates, 41 (10), 2014, pp. 7847-7882.
Lingaiah et al., Synthetic Communications, 34 (23), 2004, pp. 4431-4437.
Marchalin et al., Monatshefte für Chemie, 120, 1989, pp. 1101-1105.
Martinez-Grau, Anales de Quimica, 90, 1994, pp. 452-456.
Moustafa et al., Beilstein Journal of Organic Chemistry, 10, 2014, pp. 141-149.
Pagadala et al., Journal of Heterocyclic Chemistry, 52 (4), 2014, pp. 1226-1229.
Rad-Moghadam et al., Applied Organometallic Chemistry, 28(3), 2014, pp. 146-150.
Ramesh et al., Research of Chemical Intermediates, 41 (10), 2014, pp. 8009-8017.
Shestopalov et al. Heterocycles, 51 (5), 1999, pp. 1101-1107.
Chembank (2009) CAS RN 1136618-30-8.
Del los Ríos et al. (2002) Bioorganic & Medicinal Chemistry 10:2077-2088 "Novel Tacrine Derivatives that Block Neuronal Calcium Channels".
International Search Report and the Written Opinion for PCT/AU2016/050332 dated Aug. 10, 2016.
Kang et al. (2013) Bioorganic & Medicinal Chemistry 21:4365-4373 "Antagonism of L-type $Ca^{2+}$ channels $Ca_v1.3$ and $Ca_v1.2$ by 1,4-dihydropyrimidines and 4H-pyrans as dihydropyridine mimics".
León et al. (2005) Bioorganic & Medicinal Chemistry 13:1167-1175 "Synthesis, acetylcholinesterase inhibition and neuroprotective activity of new tacrine analogues".
Litvinov et al. (2009) Russian Chemical Bulletin, International Edition, 58(2):479-481 "Convenient selective synthesis of 5,7,8,9-tetrahydro-4H,6H-chromeno[2,3-d][1,3]oxazin-4-ones".
Marco-Contelles et al. (2006) Bioorganic & Medicinal Chemistry 14:8176-8185 "New multipotent tetracyclic tacrines with neuroprotective activity".
Zeng et al. (2012) Research on Chemical Intermediates 38:1751-1760 "Synthesis of 2-amide-3-carboxylate-4-aryl-4H-chromene derivatives".

\* cited by examiner

4H-PYRAN COMPOUNDS AS INSULIN-REGULATED AMINOPEPTIDASE (IRAP) INHIBITORS

PRIORITY DATA

This application is a 35 U.S.C. § 371 national phase application of PCT/AU2016/050332 (WO2016/179645), filed on May 6, 2016, entitled "4H-PYRAN COMPOUNDS AS INSULIN-REGULATED AMINOPEPTIDASE (IRAP) INHIBITORS", which application claims priority to and the benefit of Australian Application No. 2015901676, filed May 8, 2015, the disclosures of which are incorporated herein by reference in their entirety.

FIELD

The present disclosure relates generally, but not exclusively, to compounds and their use in therapy, to compositions and agents comprising said compounds, to methods of treatment using said compounds, and their use in the manufacture of medicaments. The disclosure further relates to inhibitors of IRAP and their use in the treatment or prevention of Alzheimer's disease and the treatment and prevention of memory and cognitive disorders.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Insulin-regulated aminopeptidase (IRAP) is a 165 kDa glycoprotein that is widely distributed in many tissues including fat, muscles, kidney, adrenal, lung and heart. In the brain, it occurs as a smaller 140 kDa protein, probably due to differential glycosylation. It is a type II integral membrane protein belonging to the M1 family of zinc-dependent metallopeptidases and possesses a large C-terminal extracellular tail which contains the catalytic site, a single transmembrane domain and a smaller N-terminal intracellular domain. Initially cloned from a rat epididymal fat pad cDNA library as a marker protein (vp165) for a specialised vesicle containing the insulin-responsive glucose transporter GLUT4 (Keller et al, 1995), the same protein was cloned concurrently from human placental cDNA library as oxytocinase, an enzyme which was thought to have an important role in degrading oxytocins (Rogi et al, 1996). The $AT_4$ receptor has also recently been identified as the transmembrane enzyme insulin regulated aminopeptidase (IRAP) via mass spectral analysis of tryptic peptides generated from $AT_4$ receptor protein purified from bovine adrenal membranes (Albiston et al, 2001). Analysis of the biochemical and pharmacological properties of IRAP confirm that it is, in fact, the $AT_4$ receptor. Although isolated by three independent groups from different tissue sources and thought to subserve distinct physiological roles, properties and characteristics of this protein remain consistent.

The $AT_4$ ligands, angiotensin IV (Ang IV), its analogues Nle-Ang IV and Norleucinal Ang IV, and the structurally distinct peptide LVV-hemorphin 7 (LVV-H7), all bind with high affinity and relative specificity to a pharmacologically distinct binding site, termed the $AT_4$ receptor. All the $AT_4$ ligands, Ang IV, Nle-Ang IV, and LVV-H7, were demonstrated in vitro to be inhibitors of the aminopeptidase activity of IRAP as assessed by cleavage of the synthetic substrate Leu-β-naphthylamide. Both Ang IV and LVV-H7 display competitive kinetics indicating that $AT_4$ ligands mediate their effects by binding to the catalytic site of IRAP. Using the same system it has also been demonstrated that although the peptides Ang IV and LVV-H7 bind to the catalytic site they are not cleaved by IRAP (Lew et al, 2003).

Central administration of the peptide $AT_4$ ligands, Ang IV, its more stable analogues, or LVV-H7, in normal animals has been shown to lead to improved performance of memory tasks in both passive avoidance and spatial learning paradigms. The initial effects were observed in the passive avoidance paradigm in rats where an intracerebro-ventricular dose (1 nmol) of Ang IV increased the latency in re-entering the dark chamber after an aversive stimulus. Chronic infusion (6 days) of an Ang IV analogue into the lateral ventricle of rats at a dose of between 0.1 and 0.5 nmol/h enhanced performance in the swim maze, a spatial memory paradigm. In the Barnes maze, another spatial learning task, treatment of rats with 100 pmoles or 1 nmol of the peptide $AT_4$ ligands, $Nle^1$-Ang IV or LVV-H7, decreased the time taken to achieve learner criteria in this paradigm. Control animals treated with artificial cerebrospinal fluid took 7 days to achieve learner criteria, whereas animals treated with $Nle^1$-Ang IV or LVV-H7, at a concentration of either 100 pmoles or 1 nmole, achieved learner criteria in 3-4 days. This observation strongly indicates that the two peptides tested not only improved memory, but also enhanced spatial learning (Lew et al, 2004).

Not only did peptide $AT_4$ ligands enhance memory and learning in normal animals, the peptides reversed memory deficits induced (1) chemically by a muscarinic antagonist or (2) mechanically by knife-cut lesion of the perforant pathway. A more stable analogue of Ang IV, Nle-Ang IV, given acutely into the lateral ventricles, reversed the memory deficits induced by the muscarinic receptor antagonist, scopolamine, in a spatial learning paradigm. In the swim maze paradigm, memory deficits induced by bilateral perforant pathway lesion can be reversed by an acute dose (1 nmol) of another Ang IV analogue, Norleucinal Ang IV. The other $AT_4$ ligand, LVV-H7, given acutely prior to the conditioning trial in the passive avoidance paradigm, has also been found to reverse the memory deficit induced by scopolamine (Albiston et al, 2004).

The mechanisms for IRAP inhibitors facilitating memory are not fully understood, but studies implicate neuroendocrine mechanisms of action. Inhibition of IRAP may extend the half-life of neuropeptides that modify learning and memory processes. A number of IRAP peptide substrates including arginine-vasopressin, oxytocin, met-enkephalin, somatostatin, dynorphin and lys-bradykinin have previously been associated with memory (Matsumoto et al, 2001). Moreover, studies have shown that peptidergic neurotransmission is altered in neurodegenerative diseases leading to memory loss. IRAP is found in high concentrations in brain regions involved in processing cognitive function including the cerebral cortex, hippocampus, basal forebrain and amygdale where it is co-expressed in neurons with the glucose transporter, GLUT4. It has recently been demonstrated that IRAP inhibitors increase activity-evoked glucose uptake into the pyramidal neurons of the hippocampus (Fernando et al, 2008). Glucose is a potent modulator of learning and memory in both humans and rodents with increases in glucose demand in the hippocampus occurring during memory processing. Therefore, one potential mechanism by which compounds may facilitate memory is through the potentiation of glucose uptake into neurons.

IRAP therefore provides a target for the development of agents which may enhance or improve memory and learning. Accordingly, inhibitors of IRAP, which may disrupt or interfere with IRAP functional activity may have useful therapeutic and/or prophylactic applications in the treatment or prevention of the causes and/or symptoms of cognitive and memory disorders.

Alzheimer's Disease (AD) is progressive neurodegenerative disorder of aging, and is characterized symptomatically by progressive dementia and personality dysfunction. The abnormal deposition of protein aggregates in the intracellular and extracellular compartments of the brain are pathological characteristics of AD leading to the loss of memory, cognitive disturbances and behavioural changes.

The extracellular deposits of amyloid plaques, consist primarily of aggregated β-amyloid protein (Aβ), whereas the intracellular deposits of neurofibrillary tangles contain the hyperphosphorylated form of the microtubule-associated protein tau. Aβ is proteolytically derived from a large membrane-spanning glycoprotein known as β-amyloid precursor protein (herein referred to as "APP") (Selkoe, 2011). A large body of current research supports the hypothesis that excessive accumulation of Aβ amyloid peptide is the initiating event that triggers neurodegeneration in both sporadic and familial AD (FAD) cases. This accumulation is caused by either overproduction, altered processing, or altered clearance of the amyloid peptide, and results in self-association and deposition of Aβ as neurotoxic fibrils (Karran et al, 2011). Neuroinflammatory processes, which occur mainly around the amyloid plaques, play an active role in AD, initially mediating an acute response that is generally considered beneficial by contributing to tissue repair but in the longer term being harmful by secreting proinflammatory cytokines (such as TNF-α and IL-1β), reactive oxygen species and nitric oxide. Tumour necrosis factor α, which is elevated in AD, is found in the location of amyloid plaques where overexpression of the cytokine is found to be neurotoxic (Janelsins et al, 2005).

Notwithstanding that the prevention and treatment of AD is the subject of intensive research activity, there remains a need for new therapies directed to the treatment and prevention of AD, not only its symptoms but also with regard to pathogenic causes, such as the unwanted or excessive accumulation and deposition of plaques and suppression of a pro-inflammatory response.

SUMMARY OF DISCLOSURE

Figure 1:
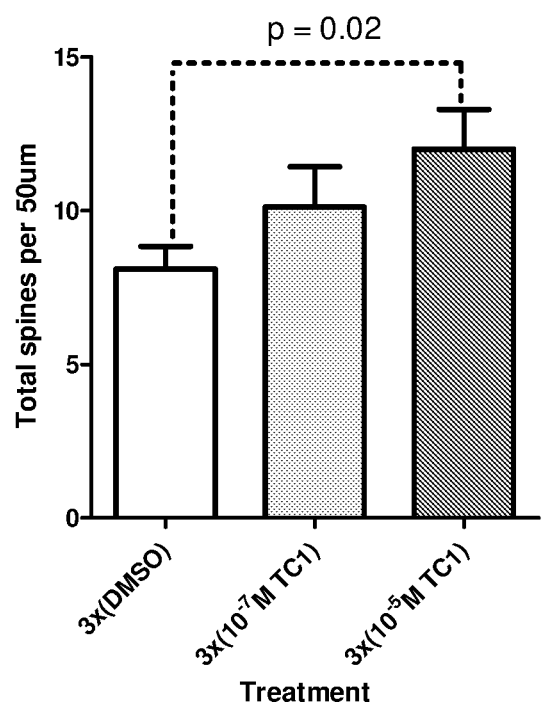
FIG. 1 graphically depicts the effect of Test Compound 1 on hippocampal spine density, a cellular correlate of memory.

It has now been found that certain 4H-pyran compounds exhibit IRAP inhibitory activity and may have utility in the treatment or prevention of conditions in which excessive, inappropriate or undesirable IRAP activity plays a role or is implicated, such as in treating and improving memory and cognition disorders, and/or in treating symptoms and/or pathological events characterized by unwanted or excessive Aβ accumulation and deposition and/or a pro-inflammatory response, such as Alzheimer's Disease.

Compounds disclosed herein are of formula (I), and their pharmaceutically acceptable salts, solvates and prodrugs:

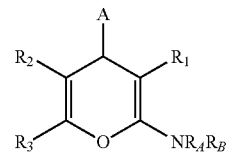

wherein
A is selected from alkyl, alkenyl, alkynyl, aryl, arylalkyl, heteroaryl, heteroarylalkyl, carbocyclyl, carbocyclylalkyl, each of which may be optionally substituted;
$R_A$ and $R_B$ are independently selected from hydrogen, alkyl and acyl;
$R_1$ is selected from CN or $CO_2R_C$;
$R_2$ is selected from $CO_2R_C$ and acyl;
$R_3$ is selected from alkyl, alkenyl, alkynyl, aryl, arylalkyl, heteroaryl, heteroarylalkyl, carbocyclyl, carbocyclylalkyl, each of which may be optionally substituted; or
$R_2$ and $R_3$ together form a 5-6-membered saturated ketocarbocyclic ring:

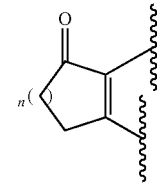

wherein n is 1 or 2;
and which ring may be optionally substituted one or more times by $C_{1-6}$alkyl; or
$R_2$ and $R_3$ together form a 5-membered lactone ring (a) or a 6-membered lactone ring (b)

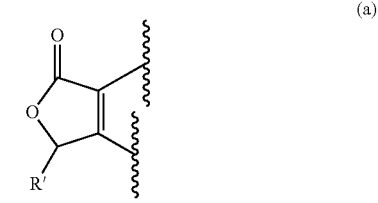

(a)

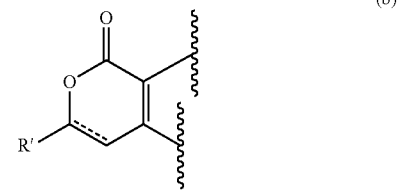

(b)

wherein ═══ is an optional double bond and R' is alkyl.
$R_C$ is selected from alkyl, alkenyl, alkynyl, aryl, arylalkyl, heteroaryl, heteroarylalkyl, carbocyclyl, carbocyclylalkyl, each of which may be optionally substituted.

In some embodiments, the disclosure provides compounds of formula (I) or pharmaceutically acceptable salts, solvates or prodrugs thereof for use in therapy.

In some further embodiments, the therapy relates to treating or preventing memory loss or impairment, or improving cognition and/or memory in a subject. In some embodiments the subject suffers from or is pre-disposed to developing Alzheimer's disease.

In some embodiments, the therapy relates to treating or preventing Alzheimer's Disease.

In an aspect, the disclosure provides a composition comprising a compound of Formula (I), or a pharmaceutically acceptable salt, solvate or prodrug thereof, and a pharmaceutically acceptable additive.

A further aspect disclosed herein provides a method of treating or preventing memory loss or impairment, or improving cognition and/or memory in a subject in need thereof comprising administering to said subject a compound of Formula (I), or a pharmaceutically acceptable salt, solvate or prodrug thereof. In some embodiments the subject suffers from or is pre-disposed to developing Alzheimer's disease.

In another aspect, there is provided a method of treating or preventing Alzheimer's disease in a subject in need thereof, comprising administering to said subject a compound of Formula (I), or a pharmaceutically acceptable salt, solvate or prodrug thereof.

Yet another aspect disclosed herein provides use of a compound of Formula (I), or a pharmaceutically acceptable salt, solvate or prodrug thereof, in the manufacture of a medicament for treating or preventing memory loss or impairment or improving cognition and/or memory in a subject. In some embodiments the subject suffers from or is pre-disposed to developing Alzheimer's disease.

Yet another aspect disclosed herein provides use of a compound of Formula (I), or a pharmaceutically acceptable salt, solvate or prodrug thereof, in the manufacture of a medicament for treating or preventing Alzheimer's disease in a subject.

In some embodiments the disclosure provides novel compounds of formula (I), salts, solvates and prodrugs thereof.

DETAILED DESCRIPTION

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers or steps.

Throughout this specification and the claims which follow, unless the context requires otherwise, the phrase "consisting essentially of", and variations such as "consists essentially of" will be understood to indicate that the recited element(s) is/are essential i.e. necessary elements of the invention. The phrase allows for the presence of other non-recited elements which do not materially affect the characteristics of the invention but excludes additional unspecified elements which would affect the basic and novel characteristics of the invention defined.

All aspects, embodiments and examples described herein are encompassed and contemplated by the term "invention".

The singular forms "a", "an" and "the" as used throughout are intended to include plural aspects where appropriate unless the context clearly dictates otherwise.

As used herein, the term "alkyl", used either alone or in compound words, denotes straight chain, or branched saturated hydrocarbon residues, preferably $C_{1-20}$ alkyl, e.g. $C_{1-10}$ or $C_{1-6}$ Some examples of straight chain and branched alkyl include methyl, ethyl, n-propyl, isopropyl, n-butyl, sec-butyl, t-butyl, n-pentyl, 1,2-dimethylpropyl, 1,1-dimethylpropyl, hexyl, 4-methylpentyl, 1-methylpentyl, 2-methyl-pentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, and decyl. Where an alkyl group is referred to generally as "propyl", butyl" etc, it will be understood that this can refer to any of straight or branched isomers where appropriate. An alkyl group may be optionally substituted by one or more optional substituents as herein defined.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1,4-pentadienyl, 1,3-hexadienyl and 1,4-hexadienyl. An alkenyl group may be optionally substituted by one or more optional substituents as herein defined.

As used herein the term "alkynyl" denotes groups formed from straight chain or branched hydrocarbon residues containing at least one carbon-carbon triple bond including ethynically mono-, di- or poly-unsaturated alkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

The term "aryl", used alone or in compound words, denotes any of mono-, bi- or polcyclic, (including conjugated and fused) hydrocarbon ring systems containing an aromatic residue. Examples of aryl include phenyl, biphenyl, terphenyl, quaterphenyl, naphthyl, tetrahydronaphthyl (tetralinyl), anthracenyl, dihydroanthracenyl, benzanthracenyl, dibenzanthracenyl, phenanthrenyl, fluorenyl, pyrenyl, idenyl, isoindenyl, indanyl, azulenyl and chrysenyl. Some particular examples of aryl include phenyl and naphthyl. An aryl group may be optionally substituted by one or more optional substituents as herein defined.

The term "carbocyclyl" includes any of non-aromatic monocyclic, bicyclic and polycyclic, (including fused, bridged or conjugated) hydrocarbon residues, e.g. $C_{3-20}$ (such as $C_{3-10}$, $C_{3-8}$ or $C_{5-6}$). The rings may be saturated, for example cycloalkyl, or may possess one or more double bonds (cycloalkenyl) and/or one or more triple bonds (cycloalkynyl). Examples of carbocyclyl include monocyclic 5-6-membered or bicyclic 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl and decalinyl. A carbocyclyl group may be optionally substituted by one or more optional substituents as herein defined. A monocarbocyclyl group may be substituted by a bridging group to form a bicyclic bridged group.

The term "heterocyclyl" when used alone or in compound words includes any of monocyclic, bicyclic, polycyclic, fused, bridged or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include, O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds. Particularly preferred heterocyclyl are monocyclic 5-6-membered and bicyclic 9-10 membered heterocyclyl. Examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl. A heterocyclyl group may be optionally substituted by one or more optional substituents as herein defined.

The term "heteroaryl" includes any of monocyclic, bicyclic, polycyclic, fused, bridged or conjugated hydrocarbon residues, wherein one or more carbon atoms are replaced by a heteroatom so as to provide an aromatic residue. Preferred heteroaryl have 3-20 ring atoms, e.g. 3-10 ring atoms. Particularly preferred heteroaryl are monocyclic 5-6-membered rings and bicyclic 9-10-membered ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridinyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinoxalinyl, quinazolinyl, quinolinyl, oxazolyl, thiazolyl, isothiazolyl, isoxazolyl, triazolyl, oxadialzolyl, oxatriazolyl, triazinyl, tetrazolyl and furazanyl. A heteroaryl group may be optionally substituted by one or more optional substituents as herein defined.

Terms written as "groupAgroupB" refer to a groupA when linked by an divalent form of group B. For example, arylalkyl, refers to an aryl group when linked by a divalent form of an alkyl group, i.e. an alkylene group.

The term "acyl" either alone or in compound words denotes a group containing the moiety C=O. In some embodiments acyl does not include a carboxylic acid, ester or amide. Acyl includes C(O)—Z, wherein Z is hydrogen or an alkyl, aryl, heteroaryl, carbocyclyl, heterocyclyl, arylalkyl, heteroarylalkyl, carbocyclylalkyl, or heterocyclylalkyl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl). The Z residue may be optionally substituted as described herein.

"Optionally substituted" means that a group, such as A, $R_3$ or $R_C$ may be unsubstituted or substituted by one or more substitutents, e.g. 1, 2, 3, 4, or 5 substituents. Examples of optional substitutents include:

alkyl, (e.g. $C_{1-6}$alkyl such as methyl, ethyl, propyl, butyl);
cycloalkyl (e.g. $C_{3-6}$cycloalkyl, such as cyclopropyl, cyclobutyl, cyclopentyl or cyclohexyl);
hydroxyalkyl (e.g. hydroxy$C_{1-6}$alkyl, such as hydroxymethyl, hydroxyethyl, hydroxypropyl);
alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl);
alkoxy (e.g. $C_{1-6}$alkoxy, such as methoxy, ethoxy, propoxy, butoxy);
alkoxyalkoxy (e.g. $C_{1-6}$alkoxy$C_{1-6}$alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy);
cycloalkoxy (e.g. cyclopropoxy, cyclobutoxy, cyclopentoxyl, cyclohexyloxy); halo;
haloalkyl, including mono-, di- and tri-haloalkyl (e.g. halo$C_{1-6}$alkyl, such as trifluoromethyl, trichloromethyl, tribromomethyl);
haloalkoxy including mono-, di- and tri-haloalkoxy (e.g. halo$C_{1-6}$alkoxy, such as trifluoromethoxy);
hydroxyl;
thiol (—SH);
alkylthio (e.g. —S$C_{1-6}$alkyl);
sulfonyl;
sulfonamido;
sulfamate;
sufamide;
sulphate;
sulfoxide;
sulfonate;
phosphate;
phosphonate;
phenyl (which itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl);
5-6 membered-heteroaryl, such as pyridyl, furyl, or thienyl, (which itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl); benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$ alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl);
phenoxy (wherein phenyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$alkoxy $C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O) $C_{1-6}$alkyl and —N($C_{1-6}$alkyl)$C_{1-6}$alkyl);
benzyloxy (wherein benzyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$alkoxy $C_{1-6}$alkoxy, halo$C_{1-6}$alkyl, halo$C_{1-6}$alkoxy, cyano, nitro, —OC(O)$C_{1-6}$ alkyl, —NH$_2$, —NH$C_{1-6}$alkyl, —NHC(O) $C_{1-6}$alkyl and —N($C_{1-6}$alkyl)$C_{1-6}$alkyl); —NH$_2$;
alkylamino (e.g. —NH$C_{1-6}$alkyl, such as methylamino, ethylamino, propylamino etc);

dialkylamino (e.g. —NH($C_{1-6}$alkyl)$_2$, such as dimethylamino, diethylamino, dipropylamino);
acylamino (e.g. —NHC(O)$C_{1-6}$alkyl, such as —NHC(O)CH$_3$);
diacylamino;
phenylamino (i.e. —NHphenyl, wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl);
benzylamino (i.e. —NHbenzyl, wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl);
nitro;
cyano;
formyl;
acyl, including —C(O)-alkyl (e.g. —C(O)$C_{1-6}$alkyl, such as acetyl);
—O—C(O)-alkyl (e.g. —OC(O)$C_{1-6}$alkyl, such as acetyloxy);
benzoyl (wherein benzyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$alkoxy $C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O) $C_{1-6}$alkyl and —N($C_{1-6}$alkyl)$C_{1-6}$alkyl);
benzoyloxy (wherein benzyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$alkoxy $C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O) $C_{1-6}$alkyl and —N($C_{1-6}$alkyl)$C_{1-6}$alkyl);
CO$_2$H;
CO$_2$alkyl (e.g. CO$_2$$C_{1-6}$alkyl such as methyl ester, ethyl ester, propyl ester, butyl ester); CO$_2$phenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl) $C_{1-6}$alkyl);
CO$_2$benzyl (wherein benzyl itself may be further substituted e.g., by one or more of $C_{1-6}$alkyl, halo, hydroxy, hydroxy $C_{1-6}$alkyl, $C_{1-6}$alkoxy, $C_{1-6}$alkoxy$C_{1-6}$alkyl, $C_{1-6}$alkoxy $C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O) $C_{1-6}$alkyl and —N($C_{1-6}$alkyl)$C_{1-6}$alkyl);
—CONH$_2$;
—C(O)NHphenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl);
—C(O)NHbenzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl);
—C(O)NHalkyl (e.g. C(O)NH$C_{1-6}$ alkyl such as methyl amide, ethyl amide, propyl amide, butyl amide);
—C(O)Ndialkyl (e.g. C(O)N($C_{1-6}$alkyl)$_2$);
aminoalkyl (e.g., HN$C_{1-6}$alkyl-, $C_{1-6}$alkylHN-$C_{1-6}$ alkyl- and ($C_{1-6}$ alkyl)$_2$N—$C_{1-6}$alkyl-); thioalkyl (e.g., HS$C_{1-6}$alkyl-);
carboxyalkyl (e.g., HO$_2$C$C_{1-6}$alkyl-);
carboxyesteralkyl (e.g., $C_{1-6}$alkylO$_2$C$C_{1-6}$alkyl-);
amidoalkyl (e.g., H$_2$N(O)C$C_{1-6}$alkyl-, H($C_{1-6}$alkyl)N(O)C$C_{1-6}$alkyl-);
formylalkyl (e.g., H(O)C$C_{1-6}$alkyl-);
acylalkyl (e.g., $C_{1-6}$alkyl(O)C$C_{1-6}$alkyl-);
acyloxy (e.g. $C_{1-6}$alkyl(O)CO—)
nitroalkyl (e.g., O$_2$N$C_{1-6}$alkyl-);
oxo (=O);
thioxo (=S);
=CHR, where R is H or $C_{1-6}$alkyl;
imino (=NR), where R is H or $C_{1-6}$alkyl;
substitution of 2 adjacent or non-adjacent carbon atoms (e.g. 1,2- or 1,3-) by one end each of a —O—(CH$_2$)$_s$—O— or —NR—(CH$_2$)$_s$—NR— group, where R is independently H or $C_{1-6}$alkyl and
s is 1 or 2; and
substitution of 2 adjacent or non-adjacent atoms independently selected from C and N by one end each of a $C_{2-5}$alkylene or alkenylene group.

The term "halogen" ("halo") denotes fluorine, chlorine, bromine or iodine (fluoro, chloro, bromo or iodo).

The term "sulfoxide" or "sulfinyl", either alone or in a compound word, refers to a group —S(O)R wherein R is selected from hydrogen, alkyl, aryl, heteroaryl, heterocyclyl, carbocyclyl, and aralkyl. Examples of R include hydrogen, $C_{1-20}$alkyl, phenyl and benzyl.

The term "sulfonyl", either alone or in a compound word, refers to a group S(O)$_2$—R, wherein R is selected from hydrogen, alkyl, aryl, heteroaryl, heterocyclyl, carbocyclyl, acyl, and aralkyl. Examples of R include hydrogen, $C_{1-20}$alkyl, phenyl and benzyl.

The term "sulfonamide", or "sulfonamyl" or "sulfonamide", either alone or in a compound word, refers to a group S(O)$_2$NRR wherein each R is independently selected from hydrogen, alkyl, aryl, heteroaryl, heterocyclyl, carbocyclyl, acyl, and aralkyl. Examples of R include hydrogen, $C_{1-20}$alkyl, phenyl and benzyl. In an embodiment at least one R is hydrogen. In another form, both R are hydrogen.

The term "sulfamate", either alone or in a compound word, refers to a group —OS(O)$_2$NRR wherein each R is independently selected from hydrogen, alkyl, aryl, heteroaryl, heterocyclyl, carbocyclyl, acyl, and aralkyl. Examples of R include hydrogen, $C_{1-20}$alkyl, phenyl and benzyl. In an embodiment at least one R is hydrogen. In another form, both R are hydrogen.

The term "sulfamide", either alone or in a compound word, refers to a group —NRS(O)$_2$NRR wherein each R is independently selected from hydrogen, alkyl, aryl, heteroaryl, heterocyclyl, carbocyclyl, acyl, and aralkyl. Examples of R include hydrogen, $C_{1-20}$alkyl, phenyl and benzyl. In an embodiment at least one R is hydrogen. In another form, both R are hydrogen.

A "sulfate" group refers to a group —OS(O)$_2$OR wherein R is selected from hydrogen, alkyl, aryl, heteroaryl, heterocyclyl, carbocyclyl, acyl, and aralkyl. Examples of R include hydrogen, $C_{1-20}$alkyl, phenyl and benzyl.

The term "sulfonate" refers to a group SO$_3$R wherein R is selected from hydrogen, alkyl, aryl, heteroaryl, heterocyclyl, carbocyclyl, acyl, and aralkyl. Examples of R include hydrogen, $C_{1-20}$alkyl, phenyl and benzyl.

The term "thio" is intended to include groups of the formula "—SR" wherein R can be hydrogen (thiol), alkyl, aryl, carbocyclyl, heteroaryl, heterocyclyl, aralkyl, and acyl. Examples of R include hydrogen, $C_{1-20}$alkyl, phenyl and benzyl.

The term, "amino" is used here in its broadest sense as understood in the art and includes groups of the formula —$NR_AR_B$ wherein $R_A$ and $R_B$ may be independently selected from hydrogen, hydroxy alkyl, alkoxyalkyl, aryl, heteroaryl, carbocyclyl, heterocyclyl, arylalkyl, heteroarylalkyl, carbocyclylalkyl, heterocyclylalkyl, acyl and amido, each of which may be optionally substituted as described herein. $R_A$ and $R_B$, together with the nitrogen to which they are attached, may also form a monocyclic, or fused polycyclic ring system e.g. a 3-10-membered ring, particularly, 5-6 and 9-10-membered systems. Examples of "amino" include —$NH_2$, —NHalkyl (e.g. —$NHC_{1-20}$alkyl), —NHalkoxyalkyl, —NHaryl (e.g. —NHphenyl), —NHaralkyl (e.g. —NHbenzyl), —NHacyl (e.g. —NHC(O)$C_{1-20}$alkyl, —NHC(O)phenyl), —NHamido, (e.g. NHC(O)NH$C_{1-6}$alkyl, NHC(O)NH phenyl), —Ndialkyl (wherein each alkyl, for example $C_{1-20}$, may be the same or different) and 5 or 6 membered rings, optionally containing one or more same or different heteroatoms (e.g. O, N and S). Reference to groups written as "[group] amino" is intended to reflect the nature of the $R_A$ and $R_B$ groups. For example, "alkylamino" refers to —$NR_AR_B$ where one of $R_A$ or $R_B$ is alkyl. "Dialkylamino" refers to —$NR_AR_B$ where $R_A$ and $R_B$ are each (independently) an alkyl group.

The term "amido" is used here in its broadest sense as understood in the art and includes groups having the formula $C(O)NR_AR^B$, wherein $R^A$ and $R^A$ are as defined as above. Examples of amido include $C(O)NH_2$, C(O)NHalkyl (e.g. $C_{1-20}$alkyl), C(O)NHaryl (e.g. C(O)NHphenyl), C(O)NHaralkyl (e.g. C(O)NHbenzyl), C(O)NHacyl (e.g. C(O)NHC(O)$C_{1-20}$alkyl, C(O)NHC(O)phenyl), C(O)Nalkylalkyl (wherein each alkyl, for example $C_{1-20}$, may be the same or different) and 5- or 6-membered rings, optionally containing one or more same or different heteroatoms (e.g. O, N and S).

The term "carboxy ester" is used here in its broadest sense as understood in the art and includes groups having the formula —$CO_2R$, wherein R may be selected from groups including alkyl, aryl, carbocyclyl, heteroaryl, heterocyclyl, arylalkyl, heteroarylalkyl, carbocyclylalkyl, heterocyclylalkyl, aralkenyl, heteroarylalkenyl, carbocyclylalkenyl, heterocyclylalkenyl, aralkynyl, heteroarylalkynyl, carbocyclylalkynyl, heterocyclylalkynyl, and acyl, each of which may be optionally substituted. Some examples of carboxy ester include —$CO_2C_{1-20}$alkyl, —$CO_2$aryl (e.g. —$CO_2$phenyl), —$CO_2arC_{1-20}$alkyl (e.g. —$CO_2$ benzyl).

The term "phosphonate" refers to a group —$P(O)(OR_2)$ wherein R is independently selected from hydrogen, alkyl, aryl, heteroaryl, heterocyclyl, carbocyclyl, acyl, and aralkyl. Examples of R include hydrogen, $C_{1-20}$alkyl, phenyl and benzyl.

The term "phosphate" refers to a group —$OP(O)(OR)_2$ wherein R is independently selected from hydrogen, alkyl, aryl, heteroaryl, heterocyclyl, carbocyclyl, acyl, and aralkyl. Examples of R include hydrogen, $C_{1-20}$alkyl, phenyl and benzyl.

Carboxylic isosteres are groups which can exhibit the same or similar properties as a carboxylic group. Some examples of carboxylic acid isosteres include: —$SO_3H$, —$SO_2NHR$, —$PO_2R_2$, —CN, —$PO_2R_2$, —OH, —OR, —SH, —SR, —NHCOR, —$NR_2$, —$CONR_2$, —CONH(O)R, —$CONHNHSO_2R$, —$COHNSO_2R$ and —CONR—CN, where R is selected from H, alkyl (such as $C_{1-10}$ alkyl, $C_{1-6}$alkyl, or $C_{1-3}$alkyl), phenyl and benzyl. Other examples of carboxylic acid isosteres include carbocyclic and heterocyclic groups such as:

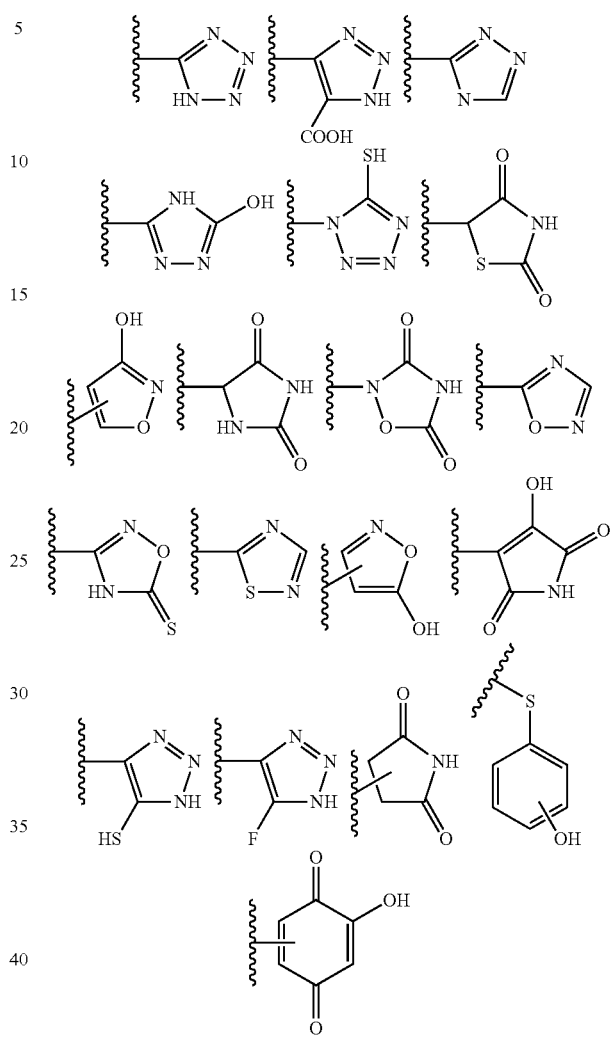

Some non-limiting embodiments of Formula (I) are described hereinafter in more detail:

(a) In some embodiments, A is unsubstituted or substituted aryl or heteroaryl group. In other embodiments, A is unsubstituted or substituted carbocyclic or heterocyclic group, for example a 5, or 6-ring membered carbocyclic or heterocyclic group. In further embodiments, A is an alkylene (e.g. $C_1$, $C_2$, $C_3$, $C_4$, $C_5$ or $C_6$) linked substituted or unsubstituted aryl or heteroaryl group or, alkylene (e.g. $C_1$, $C_2$, $C_3$, $C_4$, $C_5$ or $C_6$) linked substituted or unsubstituted carbocyclic or heterocyclic group. In some examples, A is substituted or unsubstituted phenyl, pyridinyl, quinolinyl or quinoxalinyl.

(b) In some embodiments, including any embodiments described in (a) above, A is substituted by one or more, same or different, optional substituents as described herein. In further embodiments thereof, A is unsubstituted or substituted by one or more substituents independently selected from: $CO_2H$ and carboxylic acid isosteres (including OH and CN), halo, alkoxy (e.g $C_{1-6}$alkoxy), nitro, alkyl (e.g. $C_{1-6}$alkyl) optionally substituted by hydroxyl, amino or halo, acyloxy (e.g $C_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g C(O)OC$_{1-6}$alkyl). In some particular examples, A is phenyl, pyridinyl, quinolinyl or quinoxalinyl, substituted by one or more optional substituents independently selected from: CO$_2$H and carboxylic acid isosteres (including OH and CN), halo, alkoxy (e.g C$_{1-6}$alkoxy), nitro, alkyl (e.g. C$_{1-6}$alkyl), acyloxy (e.g C$_{1-6}$acyloxy), pyridyl, thienyl, methylenedioxy and carboxy ester (e.g C(O)OC$_{1-6}$alkyl).

(c) In some embodiments, including any embodiments described in (a) and (b) above, R$_A$ and R$_B$ are both hydrogen. In other embodiments, including any embodiments described in (a) and (b) above, one of R$_A$ and R$_B$ is hydrogen and the other is alkyl (e.g. C$_{1-6}$ alkyl) or acyl (e.g. C(O)C$_{1-6}$ alkyl or C(O)phenyl). In still other embodiments, including any embodiments described in (a) and (b) above, R$_A$ and R$_B$ are independently selected from alkyl (e.g. C$_{1-6}$ alkyl) and acyl (e.g. C(O)C$_{1-6}$ alkyl and C(O)phenyl). In some particular examples A is phenyl, pyridinyl, quinolinyl or quinoxalinyl, unsubstituted or substituted by one or more substituents independently selected from: CO$_2$H and carboxylic acid isosteres (including OH and CN), halo, alkoxy (e.g C$_{1-6}$alkoxy), nitro, alkyl (e.g. C$_{1-6}$alkyl) optionally substituted by hydroxyl, amino or halo, acyloxy (e.g C$_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g C(O)OC$_{1-6}$alkyl); and R$_A$ and R$_B$ are both hydrogen, or one of R$_A$ and R$_B$ is hydrogen and the other is alkyl (e.g. C$_{1-6}$alkyl) or acyl (e.g. C(O)C$_{1-6}$ alkyl and C(O)phenyl), or R$_A$ and R$_B$ are independently selected from alkyl (e.g. C$_{1-6}$ alkyl) and acyl (e.g. C(O)C$_{1-6}$ alkyl and C(O)phenyl).

(d) In some embodiments, including any embodiments described in (a), (b) and (c) above, R$_1$ is CN. In other embodiments, including any embodiments described in (a), (b) and (c) above, R$_1$ is selected from CO$_2$C$_{1-6}$alkyl, CO$_2$C$_{1-6}$alkenyl. CO$_2$C$_{1-6}$alkynyl, CO$_2$phenyl, CO$_2$(CH$_2$)$_{1-6}$phenyl, CO$_2$5-6-membered heteroaryl, CO$_2$(CH$_2$)$_{1-6}$-5-6-membered heteroaryl, CO$_2$C$_{3-6}$cycloalkyl, and CO$_2$(CH$_2$)$_{1-6}$C$_{3-6}$cycloalkyl, each of which may be optionally substituted. In some particular examples A is phenyl, pyridinyl, quinolinyl or quinoxalinyl, unsubstituted or substituted by one or more substituents independently selected from: CO$_2$H and carboxylic acid isosteres (including OH and CN), halo, alkoxy (e.g C$_{1-6}$alkoxy), nitro, alkyl (e.g. C$_{1-6}$alkyl) optionally substituted by hydroxyl, amino or halo, acyloxy (e.g C$_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g C(O)OC$_{1-6}$alkyl); and R$_A$ and R$_B$ are both hydrogen, or one of R$_A$ and R$_B$ is hydrogen and the other is alkyl (e.g. C$_{1-6}$ alkyl) or acyl (e.g. C(O)C$_{1-6}$ alkyl or C(O)phenyl), or R$_A$ and R$_B$ are independently selected from alkyl (e.g. C$_{1-6}$ alkyl) and acyl (e.g. C(O)C$_{1-6}$ alkyl and C(O)phenyl); and R$_1$ is CN or CO$_2$C$_{1-6}$alkyl.

(e) In some embodiments, including any embodiments described in (a), (b), (c) and (d) above, R$_2$ is. CO$_2$C$_{1-6}$alkyl, CO$_2$C$_{1-6}$alkenyl. CO$_2$C$_{1-6}$alkynyl, CO$_2$phenyl, CO$_2$(CH$_2$)$_{1-6}$Phenyl, CO$_2$5-6-membered heteroaryl, CO$_2$(CH$_2$)$_{1-6}$-5-6-membered heteroaryl, CO$_2$C$_{3-6}$cycloalkyl, CO$_2$(CH$_2$)$_{16}$C$_{3-6}$cycloalkyl, C(O)C$_{1-6}$alkyl, C(O)C$_{1-6}$alkenyl. C(O)C$_{1-6}$alkynyl, C(O)phenyl, C(O)(CH$_2$)$_{1-6}$phenyl, C(O)5-6-membered C(O)heteroaryl, C(O)(CH$_2$)$_{1-6}$-5-6-membered heteroaryl, C(O)C$_{3-6}$cycloalkyl, or C(O)(CH$_2$)$_{1-6}$C$_{3-6}$cycloalkyl, each of which may be optionally substituted. In some particular examples A is phenyl, pyridinyl, quinolinyl or quinoxalinyl, unsubstituted or substituted by one or more substituents independently selected from: CO$_2$H and carboxylic acid isosteres (including OH and CN), halo, alkoxy (e.g C$_{1-6}$alkoxy), nitro, alkyl (e.g. C$_{1-6}$alkyl) optionally substituted by hydroxyl, amino or halo, acyloxy (e.g C$_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g C(O)OC$_{1-6}$alkyl); and R$_A$ and R$_B$ are both hydrogen, or one of R$_A$ and R$_B$ is hydrogen and the other is alkyl (e.g. C$_{1-6}$ alkyl) or acyl (e.g. C(O)C$_{1-6}$ alkyl and C(O)phenyl), or R$_A$ and R$_B$ are independently selected from alkyl (e.g. C$_{1-6}$ alkyl) and acyl (e.g. C(O)C$_{1-6}$ alkyl and C(O)phenyl); and R$_1$ is CN or CO$_2$C$_{1-6}$alkyl; R$_2$ is CO$_2$C$_{1-6}$alkyl or CO$_2$benzyl or C(O)C$_{1-6}$alkyl.

(f) In some embodiments, including any one of (a), (b), (c), (d) and (e) above R$_3$ is alkyl, such as C$_{1-6}$ alkyl. In some embodiments, including any one of (a), (b), (c), (d) and (e) above R$_3$ is C$_{1-6}$alkyl, C$_{1-6}$alkenyl. C$_{1-6}$alkynyl, phenyl, (CH$_2$)$_{1-6}$phenyl, 5-6-membered heteroaryl (CH$_2$)$_{1-6}$-5-6-membered heteroaryl, C$_{3-6}$cycloalkyl, and (CH$_2$)$_{1-6}$C$_{3-6}$cycloalkyl, each of which may be optionally substituted. In some particular examples A is phenyl, pyridinyl, quinolinyl or quinoxalinyl, unsubstituted or substituted by one or more substituents independently selected from: CO$_2$H and carboxylic acid isosteres (including OH and CN), halo, alkoxy (e.g C$_{1-6}$alkoxy), nitro, alkyl (e.g. C$_{1-6}$alkyl) optionally substituted by hydroxyl, amino or halo, acyloxy (e.g C$_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g C(O)OC$_{1-6}$alkyl); and R$_A$ and R$_B$ are both hydrogen, or one of R$_A$ and R$_B$ is hydrogen and the other is alkyl (e.g. C$_{1-6}$ alkyl) or acyl (e.g. C(O)C$_{1-6}$ alkyl and C(O)phenyl), or R$_A$ and R$_B$ are independently selected from alkyl (e.g C$_{1-6}$ alkyl.) and acyl (e.g. C(O)C$_{1-6}$ alkyl and C(O)phenyl); and R$_1$ is CN or CO$_2$C$_{1-6}$alkyl; R$_2$ is CO$_2$C$_{1-6}$alkyl or CO$_2$benzyl or C(O)C$_{1-6}$alkyl; and R$_3$ is alkyl, such as C$_{1-6}$ alkyl.

(g) In some embodiments, including any embodiments described in (a), (b), (c) and (d) above, R$_2$ and R$_3$ together form a 5- or 6-membered keto-carbocyclic ring (a) which may be substituted one or more times by C$_{1-6}$alkyl. In some particular examples A is phenyl, pyridinyl, quinolinyl or quinoxalinyl, unsubstituted or substituted by one or more substituents independently selected from: CO$_2$H and carboxylic acid isosteres (including OH and CN), halo, alkoxy (e.g C$_{1-6}$alkoxy), nitro, alkyl (e.g. C$_{1-6}$alkyl) optionally substituted by hydroxyl, amino or halo, acyloxy (e.g C$_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g C(O)OC$_{1-6}$alkyl); and R$_A$ and R$_B$ are both hydrogen, or one of R$_A$ and R$_B$ is hydrogen and the other is alkyl (e.g. C$_{1-6}$ alkyl) or acyl (e.g. C(O)C$_{1-6}$ alkyl) and C(O)phenyl), or R$_A$ and R$_B$ are independently selected from alkyl (e.g. C$_{1-6}$ alkyl) and acyl (e.g. C(O)C$_{1-6}$ alkyl and C(O)phenyl); and R$_1$ is CN or CO$_2$C$_{1-6}$alkyl; and R$_2$ and R$_3$ together form a 5- or 6-membered keto-carbocyclic ring (a) which may be substituted one or more times by C$_{1-6}$alkyl.

(h) In some embodiments, including any one of (a), (b), (c) and (d) above, R$_2$ and R$_3$ together form a 5-6-membered saturated keto-carbocyclic ring:

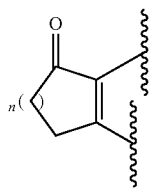

wherein n is 1 or 2;
and which ring may be optionally substituted one or more times by $C_{1-6}$alkyl; or
a 5-membered lactone ring (a) or a 6-membered lactone ring (b)

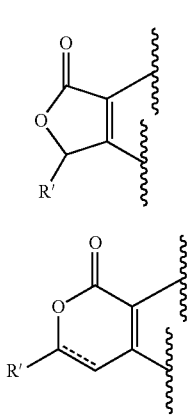

wherein ==== is an optional double bond and R' is alkyl, such as $C_{1-6}$ alkyl. In some particular examples A is phenyl, pyridinyl, quinolinyl or quinoxalinyl, unsubstituted or substituted by one or more substituents independently selected from: $CO_2H$ and carboxylic acid isosteres (including OH and CN), halo, alkoxy (e.g $C_{1-6}$alkoxy), nitro, alkyl (e.g. $C_{1-6}$alkyl) optionally substituted by hydroxyl, amino or halo, acyloxy (e.g $C_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g $C(O)OC_{1-6}$alkyl); and $R_A$ and $R_B$ are both hydrogen, or one of $R_A$ and $R_B$ is hydrogen and the other is alkyl (e.g. $C_{1-6}$ alkyl) or acyl (e.g. $C(O)C_{1-6}$ alkyl and C(O)phenyl), or $R_A$ and $R_B$ are independently selected from alkyl (e.g. $C_{1-6}$ alkyl) and acyl (e.g. $C(O)C_{1-6}$ alkyl and C(O)phenyl); and $R_1$ is CN or $CO_2C_{1-6}$alkyl; and $R_2$ and $R_3$ together form a 5-6-membered saturated keto-carbocyclic ring or a 5-membered lactone ring (a) or a 6-membered lactone ring (b), wherein R' is alkyl, such as $C_{1-6}$ alkyl.

In some further embodiments, $R_A$ and $R_B$ are both hydrogen, $R_1$ is CN or $CO_2C_{1-6}$ alkyl, $R_2$ is $CO_2C_{1-6}$alkyl or $CO_2$benzyl and $R_3$ is $C_{1-6}$alkyl. In still further examples of such embodiments A is optionally substituted phenyl. In still further examples thereof, the phenyl group is substituted with $CO_2H$ or a carboxylic acid isostere.

In some other embodiments, $R_A$ and $R_B$ are both hydrogen or one of $R_A$ and $R_B$ is acyl, such as $C(O)C_{1-6}$alkyl, $R_1$ is CN or $CO_2C_{1-6}$ alkyl, $R_2$ is acyl, such as $C(O)C_{1-6}$alkyl, and $R_3$ is $C_{1-6}$alkyl. In still further examples of such embodiments A is optionally substituted phenyl. In still further examples thereof, the phenyl group is substituted with $CO_2H$ or a carboxylic acid isostere.

In some other embodiments, $R_A$ and $R_B$ are both hydrogen or one of $R_A$ and $R_B$ is acyl, such as $C(O)C_{1-6}$alkyl, $R_1$ is CN or $CO_2C_{1-6}$ alkyl and $R_2$ and $R_3$ together form a 5- or 6-membered ketocarbocyclic ring. In still further examples of such embodiments A is optionally substituted phenyl. In still further examples thereof, the phenyl group is substituted with $CO_2H$ or a carboxylic acid isostere.

In some embodiments, the compound is of the general formula 11, 12, 13, 14, 15 or 17, as depicted in Tables 2-1, 2-2, 2-3, 2-4, 2-5, and 2-7, wherein A, $R_3$, $R_2$' and $R_1$ are as per any aspect or embodiment described herein, Thus, in some examples of general formula 11, 13, 14 and 15, Ar is a substituted or unsubstituted aryl or heteroaryl group. In other embodiments, A is a substituted or unsubstituted carbocyclic or heterocyclic group, for example, a 5- or 6-ring membered carbocyclic or heterocyclic group. In further embodiments, A is an alkylene (e.g. $C_1$, $C_2$, $C_3$, $C_4$, $C_5$ or $C_6$) linked substituted or unsubstituted aryl or heteroaryl group or, alkylene (e.g. $C_1$, $C_2$, $C_3$, $C_4$, $C_5$ or $C_6$) linked substituted or unsubstituted carbocyclic or heterocyclic group. In some examples, A is substituted or unsubstituted phenyl, pyridinyl, quinolinyl or quinoxalinyl. In still further examples, A is unsubstituted or substituted by one or more substituents selected from $CO_2H$, and carboxylic acid isosteres, (including OH and CN), halo, alkoxy (e.g $C_{1-6}$alkoxy), nitro, alkyl (e.g. $C_{1-6}$alkyl) optionally substituted by hydroxyl, amino or halo, acyloxy (e.g $C_{1-6}$acyloxy), 5-6-membered heteroaryl (such as 2, -3- and 4-pyridyl, pyridazinyl, pyrimidinyl, pyrazinyl, thiazolyl, isothiazolyl, triazolyl, oxadiazolyl, furazanyl, thiadiazolyl, pyrrolyl, thienyl, and furanyl), methylenedioxy and carboxy ester (e.g $C(O)OC_{1-6}$alkyl).

Compounds contemplated herein can be purchased through commercial sources (for example, Specs, Interbioscreen Ltd and Chembridge Corporation) or synthesized. Methods for the synthesis of 4H-pyrans are known in the art of synthetic organic chemistry and may be readily performed by the skilled addressee utilizing appropriately substituted or protected starting materials. Thus, 4H-pyrans may be prepared by reaction of a suitably substituted or functionalized aldehyde, A-CHO, with an alkylcyanoacetate or malononitrile, and a suitably substituted or functionalized di-keto compound in a one- or two-step process. Alternatively, suitably substituted or functionalized 1,5-diketo compounds may be cyclised under appropriate conditions. Some exemplary methods which may be utilized or adapted are described in Quinterio et al., *J. Heterocyclic Chemistry*, 15, 57-61, 1978; Elnagdi et al, *Journal für Praktische Chemie.*, 331, 971-976 1989; Banerjee et al., *Tetrahedron Letters*, 52, 1878-1881, 2011; Blinokhvatov et al, *Chemistry of Heterocyclic Compounds*, 28, 266-268, 1992; and Piao et al, *Tetrahedron Letters* 38, 5301-5302, 1997.

It will be recognised that in certain circumstances it may be necessary to convert or transform one substituent or functional group to another in order to arrive at the desired compound. Suitable transformations are well known and are described in references such as *Comprehensive Organic Transformation, A Guide to Functional Group Preparations*. R. C. Larock, VCH, $2^{nd}$ Edition, 1999 and *Advanced Organic Chemistry, Reactions, Mechanisms and Structure*, M. B. Smith and J. March, $6^{th}$ Edition.

It will be recognised that during the processes for the preparation of compounds contemplated by the present invention, it may be necessary or desirable to protect certain functional groups which may be reactive or sensitive to the reaction or transformation conditions undertaken. Examples of such groups include: OH (including diols), $NH_2$, $CO_2H$, SH and C=O. Suitable protecting groups for such functional groups are known in the art and may be used in accordance with standard practice. As used herein, the term "protecting group", refers to an introduced functionality which temporarily renders a particular functional group inactive under certain conditions. Such protecting groups and methods for their installation and subsequent removal at an appropriate stage are described in *Protective Groups in Organic Chemistry*, 3$^{rd}$ Edition, T. W. Greene and P. G. Wutz, John Wiley and Sons, 1999. Exemplary forms of protected groups include:

for amino (NH$_2$)—carbamates (such as Cbz, Boc, Fmoc), benzylamines, acetamides (e.g. acetamide, trifluoroacetamide);

for carbonyl—acetals, ketals, dioxanes, dithianes, and hydrazones;

for hydroxy—ethers (e.g. alkyl ethers, alkoxylalkyl ethers, allyl ethers, silyl ethers, benzyl ethers, tetrahydropyranyl ethers), carboxylic acid esters, acetals (e.g. acetonide and benzylidene acetal);

for thio (SH)—ethers (e.g. alkyl ethers, benzyl ethers), esters; and for CO$_2$H—esters (e.g. alkyl esters, benzyl esters).

It will also be recognised that certain compounds of Formula (I) may possess asymmetric centres and are therefore capable of existing in more than one stereoisomeric form, such as enantiomers and diastereomers. The invention thus also relates to optically active compounds and compounds in substantially pure isomeric form at one or more asymmetric centres, e.g., enantiomers having greater than about 90% ee, such as about 95% or 97% ee or greater than 99% ee, as well as mixtures, including racemic mixtures, thereof. Such isomers may be prepared by asymmetric synthesis, for example using chiral intermediates, enzymes, or mixtures may be resolved by conventional methods, e.g., chromatography, recrystallization, or use of a resolving agent.

Some examples of compounds of formula (I) are depicted below:

11

| Compound | A |
|---|---|
| 11a | 3-bromo-4-hydroxy-5-methoxyphenyl |
| 11b | 3-methoxy-4-hydroxyphenyl |
| 11c | 3-methoxyphenyl |
| 11d | 3-bromophenyl |
| 11e | 4-hydroxyphenyl |
| 11f | 3-bomo-4-methoxyphenyl |
| 11g | 3,4-methylenedioxyphenyl |
| 11h | 3,4-methylenedioxy-5-methoxyphenyl |
| 11i | 3,4-dimethoxyphenyl |
| 11j | 4-cyanophenyl |
| 11k | 4-carboxyphenyl |
| 11l | 4-nitrophenyl |
| 11m | 3-carboxyphenyl |
| 11n | 3-methyl-4-acetoxyphenyl |
| 11o | 3,5-dimethoxy-4-acetoxyphenyl |
| 11p | 4-(pyrid-2-yl)-phenyl |
| 11q | pyridin-3-yl |
| 11r | pyridin-4-yl |
| 11s | quinolin-2-yl |
| 11t | quinolin-3-yl |
| 11u | quinolin-4-yl |

12

| Compound | R3 | R$_2$' |
|---|---|---|
| 12a | Et | OCH$_3$ |
| 12b | Pr | OCH$_3$ |
| 12c | Et | OEt |

13

| Compound | A |
|---|---|
| 13a | 3,4-dimethoxyphenyl |
| 13b | 4-carboxyphenyl |
| 13c | 4-hydroxyphenyl |
| 13d | 3-methoxy-4-hydroxyphenyl |

14

| Compound | A |
|---|---|
| 14a | 3,4-dimethoxyphenyl |
| 14b | 4-carboxyphenyl |
| 14c | 4-methoxycarbonylphenyl |
| 14d | 4-cyanophenyl |
| 14e | 3-cyanophenyl |

15

| Compound | A |
|---|---|
| 15a | 4-carboxyphenyl |
| 15b | 3-carboxyphenyl |
| 15c | 3-methoxy-4-hydroxyphenyl |
| 15d | 4-cyanophenyl |
| 15e | 3-cyanophenyl |
| 15f | 4-methoxycarbonylphenyl |
| 15g | 4-(thiophen-2-yl)phenyl |
| 15h | pyridin-3-yl |
| 15i | quinolin-2-yl |

-continued

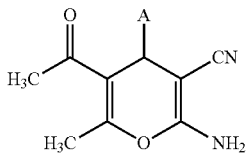

Compound A

| | A |
|---|---|
| 15j | quinoxalin-6-yl |
| 15k | 2-carboxyphenyl |

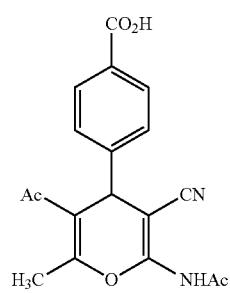

Compound 16

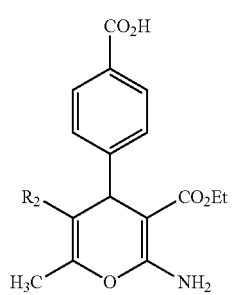

Compound R₂

| | R₂ |
|---|---|
| 17a | CO₂Et |
| 17b | Ac |

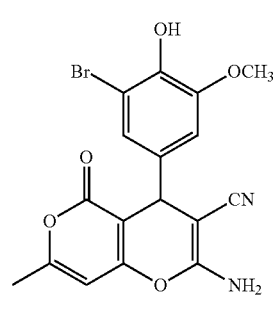 [SMILES: COc1cc(C2C(C#N)=C(N)Oc3cc(C)oc(=O)c32)cc(Br)c1O]

Compound 18

As used herein, the term "inhibit" or variations thereof when used in relation to IRAP activity, such as aminopeptidase activity, includes prevention, interruption, disruption, reduction, retardation or otherwise decrease in the rate or extent of IRAP activity, and thus includes partial inhibition of IRAP activity as well as complete or near complete inhibition.

The level of IRAP inhibitory activity of the compounds disclosed herein can be initially determined in an in vitro assay, which measures the ability of the test compound to inhibit the aminopeptidase activity of IRAP, by assessing the rate or extent of cleavage or degradation of an IRAP aminopeptidase substrate such as Leu-β-naphthylamide or Leu-4-methylcoumaryl-7-amide. Comparison can then be made to a control assay, whereby the rate or extent of cleavage is determined in the absence of the compound. A comparative reduction in the rate or extent of cleavage of the substrate in the presence of the compound can be taken to be a measure of the inhibitory effect of the compound.

Thus, there is also provided a method of determining the IRAP inhibitory activity of a compound, comprising:
(a) incubating IRAP, an IRAP substrate and a compound as described herein; and
(b) assessing the rate or extent of cleavage of the substrate; wherein a reduction or inhibition in the rate or extent of cleavage of the substrate, when compared to a control, is indicative of IRAP inhibitory activity of the compound.

Advantageously, in one or more embodiments of the disclosure, a compound of Formula (I), or a pharmaceutically acceptable salt, prodrug or solvate thereof, may exhibit selectivity or specificity for IRAP over other enzymes.

Disorders and conditions where undesirable or excessive IRAP aminopeptidase activity is implicated or involved may include memory or learning disorders associated with Alzheimer's disease and other forms of dementia and memory loss (be they age-related, induced through head trauma, hypoxic damage, surgery, cerebral infarcts or chemical means such as neurotoxins). It should also be appreciated that the compounds of the present invention may also be useful in enhancing or improving memory or learning in normal individuals, i.e. those not suffering from cognitive pathologies such as those described above.

In addition to improving memory or cognitive performance, compounds of formula (I) may also prevent or treat causal pathologies of Alzheimer's disease, for example by preventing or effecting a reduction in the accumulation of intra and/or extra cellular deposition of proteinaceous tangles or plaques.

Memory or learning (e.g. spatial learning) enhancement refers to an improvement in the ability of a subject to memorize or learn information and can be determined by well established tests. A positive improvement in the "score" or result obtained in such a test compared to a score/result obtained prior to administration of the compounds is taken to be an enhancement in memory or learning as appropriate. In certain embodiments of the invention, the improvement can be expressed as a % (score after administration of compound/score prior to administration of compound) and may represent an improvement of at least about 10%, 20%, 25%, 40%, 50%, 60%, 70%, 80%, 90%, 100%, 150% or 200% or more.

A number of well known and established tests exist for laboratory animals and rats and mice can be tested using these, which include the Barnes Maze paradigm (Greferath et al., 2000), Barnes Circular Maze test (Lee et al., 2004) or modifications thereof, the Y maze test, or passive avoidance test. Suitable protocols are briefly outlined herein in the Examples Memory and learning can be tested in humans by any one of a number of well established neuropsychological tests such as California Verbal Learning Test, Wechsler Memory Scale-III, Hopkins Verbal Learning Test—Revised™, Rey Auditory Verbal Learning Test, and Rey-Osterrieth Complex Figure Design Test.

Subjects to be treated include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention.

The compounds contemplated herein may be administered to a subject in a treatment, or preventing effective amount, which is intended to include an amount which, when administered according to the desired dosing regimen, at least partially attains the desired effect. Treatment includes one or more of: improving, alleviating, eliminating, reversing (partially or altogether), inhibiting the progression of or reducing the frequency of, one or more symptoms or causal pathologies of the particular disorder or condition being treated. Prevention includes preventing, halting or delaying the onset of, or progression of one or more symptoms or causal pathologies of the particular disorder or condition.

Suitable dosage amounts and dosing regimens can be determined by the attending physician and may depend on the particular condition being treated, the severity of the condition as well as the general age, health and weight of the subject. Suitable dosage amounts may lie in the range of from 1 μg to 1 g of compound, salt or solvate, for example, 1 μg-1 mg, 1 mg-10 mg, 10 mg-50 mg, 50 mg-100 mg or 100 mg-500 mg. Dosages may be administered once, or multiple times daily, or one or more times weekly, fortnightly or monthly.

The active ingredient may be administered in a single dose or a series of doses. While it is possible for the active ingredient to be administered alone, it is preferable to present it as a composition, preferably as a pharmaceutical composition, with one or more pharmaceutically acceptable additives. The compounds disclosed herein may be administered as the sole therapeutic agent for the disease or condition being treated or prevented or improved, but may also be administered in conjunction with one or more other therapies and/or therapeutic agents, either contemporaneously, or at separate times, as a single composition or separate compositions as appropriate. Thus, the disclosure also provides for combinations and compositions containing a compound of Formula (I), or a pharmaceutically acceptable salt, prodrug or solvate thereof, as the only therapeutic agent, and one or more additional therapeutic agents for treating or preventing memory loss or impairment, or improving cognition and/or memory in a subject, or treating or preventing Alzheimer's disease.

The formulation of such compositions is well known to those skilled in the art, see for example, *Remington's Pharmaceutical Sciences*, 21$^{st}$ Edition, Mack Publishing, 2005. The composition may contain any suitable additives, carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The additive must be pharmaceutically acceptable in the sense of being compatible with the other ingredients of the composition and not injurious to the subject. Compositions include those suitable for oral, rectal, nasal, topical (including dermal, buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the additive which constitutes one or more accessory ingredients. In general, the compositions are prepared by uniformly and intimately bringing into association the active ingredient with liquid additive or finely divided solid additive or both, and then if necessary shaping the product.

Compositions of the present disclosure suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Devices for transdermal delivery, such as patches, may also be used to administer the compounds of the invention.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other additives or agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The present invention also relates to prodrugs of Formula (I). Any compound that is a prodrug of a compound of Formula (I) is within the scope and spirit of the invention. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as phosphonate, sulphonate and carboxy esters, such as an acetate, or thioester or where a free amino group is converted into an amide such as a carboxy, phosphonate or sulphonate amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, Adv. BioSci., 1979, 20, 369, Kyncl, J. et al), enamines (see, for example, J. Pharm. Sci., 1971, 60, 1810, Caldwell, H. et al), Schiff bases (see, for example, U.S. Pat. No. 2,923,661 and Antimicrob. Agents Chemother., 1981, 19, 1004, Smyth, R. et al), oxazolidines (see, for example, J. Pharm. Sci, 1983, 72, 1294, Johansen, M. et al), Mannich bases (see, for example, J. Pharm. Sci. 1980, 69, 44, Bundgaard, H. et al and J. Am. Chem. Soc., 1959, 81, 1198, Gottstein, W. et al), hydroxymethyl derivatives (see, for example, J. Pharm. Sci, 1981, 70, 855, Bansal, P. et al) and N-(acyloxy)alkyl derivatives and carbamates (see, for example, J. Med. Chem., 1980, 23, 469, Bodor, N. et al, J. Med. Chem., 1984, 27, 1037, Firestone, R. et al, J. Med. Chem., 1967, 10, 960, Kreiger, M. et al, U.S. Pat. No. 5,684,018 and J. Med. Chem., 1988, 31, 318-322, Alexander, J. et al). Other conventional procedures for the selection and preparation of suitable prodrugs are known in the art and are described, for example, in WO 00/23419; Design of Prodrugs, H. Bundgaard, Ed., Elsevier Science Publishers, 1985; Methods in Enzymology, 42: 309-396, K. Widder, Ed, Academic Press, 1985; A Textbook of Drug Design and Development, Krogsgaard-Larsen and H. Bundgaard, Eds, Chapter 5, p 113-191 (1991); Advanced Drug Delivery Reviews, 8; 1-38 (1992); Journal of Pharmaceutical Sciences, 77; 285 (1988), H. Bundgaard, et al; Chem Pharm Bull, 32692 (1984), N. Kakeya et al and The Organic Chemistry of Drug Design and Drug Action, Chapter 8, pp 352-401, Academic press, Inc., 1992.

Suitable pharmaceutically acceptable salts of compounds of Formula (I) may include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, o-(p-hydroxybenzoyl)benzoic, 4'-4''-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides or dialkyl sulfates such as dimethyl and diethyl sulfate.

The compounds of the invention may be in crystalline form either as the free compounds or as solvates and it is intended that both forms are within the scope of the present invention. The term "solvate" refers to a complex or aggregate formed by one or more molecules of a solute, i.e. compounds contemplated by the invention, and one or more molecules of a solvent. Suitable solvents are well understood in the art and include for example, of water, i.e. to form hydrates, and common organic solvents such as alcohols (methanol, ethanol, isopropanol) and acetic acid. Methods of solvation are generally known within the art, for example, recrystallization from an appropriate solvent.

The compounds of the invention may also be presented for use in veterinary compositions. These may be prepared by any suitable means known in the art. Examples of such compositions include those adapted for:

(a) oral administration, external application (e.g. drenches including aqueous and non-aqueous solutions or suspensions), tablets, boluses, powders, granules, pellets for admixture with feedstuffs, pastes for application to the tongue;

(b) parenteral administration, e.g. subcutaneous, intramuscular or intravenous injection as a sterile solution or suspension;

topical application e.g. creams, ointments, gels, lotions etc.

The disclosure is now further illustrated by the following examples which are included for the purpose of illustrating some embodiments thereof and are not intended to limit the generality hereinbefore described.

EXAMPLES

Example 1—Chemical Synthesis

All reagents and solvents were used as received. Proton nuclear magnetic resonance ($^1$H n.m.r.) spectra were recorded at 300 MHz with a Bruker Advance DPX-300 or at 400 MHz using a Bruker Ultrashield-Advance III NMR spectrometer. The $^1$H n.m.r. spectra refer to solutions in deuterated solvents as indicated. The residual solvent peaks have been used as an internal reference, with each resonance assigned according to the following convention: chemical shift (δ) measured in parts per million (ppm) relative to the residual solvent peak. High Resolution Mass Spectometry analyses were collected on a Bruker Apex II Fourier Transform Ion Cyclotron Resonance Mass Spectometer fitted with an electrospray ion source (ESI). Low Resolution Mass Spectrometry analyses were performed using a Micromass Platform II single quadropole mass spectrometer equipped with an atmospheric pressure (ESI/APCI) ion source. Liquid Chromatography Mass Spectra (LCMS) were measured on a Shimadzu 2020 LCMS system incorporating a photodiode array detector (214 nm unless otherwise stated) coupled directly into an electrospray ionisation source and a single quadrupole mass analyser. Standard RP-HPLC was carried out at room temperature employing a Phenomenex Luna C8 (100×2.0 mm I.D.) column eluting with a gradient of 0-64% $CH_3CN$ in 0.05% aqueous trifluoroacetic acid over 10 min at a flow rate of 0.2 ml/min unless stated otherwise. Mass spectra were obtained in positive mode with a scan range of 200-2000 m/z. Analytical HPLC was performed on a Waters 2690 HPLC system incorporating a diode array detector (254 nm), employing a Phenomenex column (Luna C8(2), 100×4.5 mm ID) eluting with a gradient of 16-80% acetonitrile in 0.1% aqueous trifluoroacetic acid, over 10 minutes at a flow rate of 1 ml/min. Analytical thin layer chromatography (t.l.c.) was performed on Merck aluminium sheets coated in silica gel 60 $F_{254}$ and visualization accomplished with a UV lamp. Column chromatography was carried out using silica gel 60 (Merck). Purity of compounds (>95%) was established by either reverse phase HPLC or $^1$H n.m.r.

General Method

Piperidine (cat.) was added to a solution of malononitrile (1.1 eq.) and aldehyde (1 eq.) in EtOH (3-5 mL) and stirred at ambient temperature for 15 min. Ethyl acetoacetate (1.1 eq.) was added and the mixture stirred at ambient temperature for 4 hrs. The volume of solvent was reduced and the resulting precipitate was collected and washed with cold EtOH to give the title compound. If required, the compound was recrystallised from hot EtOH or triturated with DCM.

(a) 4-(2-Amino-3-cyano-5-(ethoxycarbonyl)-6-methyl-4H-pyran-4-yl)benzoic Acid (11k)

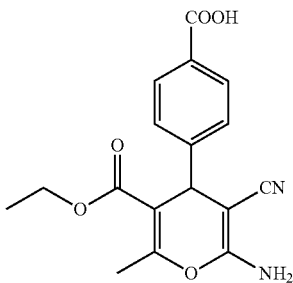 [SMILES: CCOC(=O)C1=C(C)OC(N)=C(C#N)C1c1ccc(C(=O)O)cc1]

Following the general method, 4-carboxybenzaldehyde (1.0 g, 6.6 mmol), malononitrile (0.48 g, 7.3 mmol), ethyl acetoacetate (0.95 g, 7.3 mmol), piperidine (8 drops), and ethanol (20 mL), gave the title compound as a white solid (1.7 g, 78%). $^1$H NMR (300 MHz, MeOH) δ 7.96 (d, J=7.2 Hz, 2H), 7.29 (d, J=7.2 Hz, 2H), 4.46 (s, 1H), 4.02 (q, J=6.9 Hz, 2H), 2.39 (s, 3H), 1.08 (t, J=6.7 Hz, 3H). MS (ESI) m/z: 329.4 (M+H)$^+$ (65%).

(b) 3-(2-Amino-3-cyano-5-(ethoxycarbonyl)-6-methyl-4H-pyran-4-yl)benzoic Acid (11m)

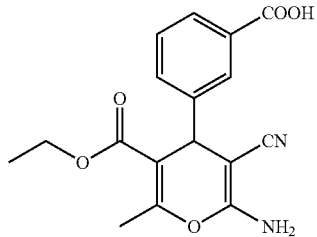 [SMILES: CCOC(=O)C1=C(C)OC(N)=C(C#N)C1c1cccc(C(=O)O)c1]

Following the general method, 3-carboxybenzaldehyde (100 mg, 0.66 mmol), malononitrile (48 mg, 0.73 mmol), ethyl acetoacetate (95 mg, 0.73 mmol), piperidine (drops), and ethanol (3 mL), gave the title compound after recrystallistation from EtOH as a white solid (41 mg, 19%). $^1$H NMR (600 MHz, MeOD) δ 7.89 (d, J=7.2 Hz, 1H), 7.86 (s, 1H), 7.45-7.41 (m, 2H), 4.46 (s, 1H), 4.07-3.98 (m, 2H), 2.39 (s, 3H), 1.09 (t, J=7.1 Hz, 3H). MS (ESI) m/z: 329.4 (M+H)$^+$ (80%).

(c) Ethyl 4-(4-acetoxy-3-methylphenyl)-6-amino-5-cyano-2-methyl-4H-pyran-3-carboxylate (11n)

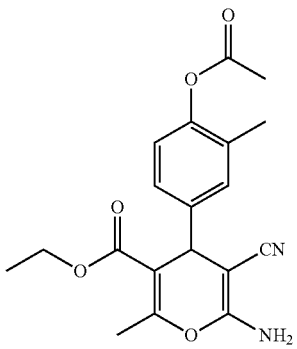 [SMILES: CCOC(=O)C1=C(C)OC(N)=C(C#N)C1c1ccc(OC(C)=O)c(C)c1]

Following the general method, 4-formyl-2-methylphenyl acetate (100 mg, 0.56 mmol), malononitrile (41 mg, 0.67 mmol), ethyl acetoacetate (80 mg, 0.67 mmol), piperidine (3 drops), and ethanol (5 mL), gave the title compound as a white solid (87 mg, 44%). $^1$H NMR (300 MHz, CDCl$_3$) δ 7.04-6.99 (m, 2H), 6.93 (d, J=7.9 Hz, 1H), 4.46 (bs, 2H), 4.41 (s, 1H), 4.15-3.95 (m, 2H), 2.37 (s, 3H), 2.29 (s, 3H), 2.14 (s, 3H), 1.12 (t, J=7.1 Hz, 3H). MS (ESI) m/z: 357.3 (M+H)$^+$ (50%); 713.6 (2M+H)$^+$ (100%).

(d) Ethyl 4-(4-acetoxy-3,5-dimethylphenyl)-6-amino-5-cyano-2-methyl-4H-pyran-3-carboxylate (11o)

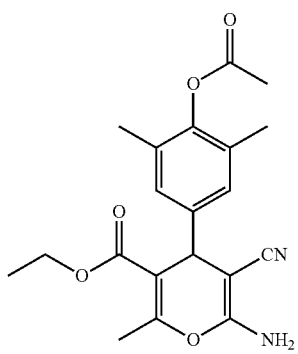 [SMILES: CCOC(=O)C1=C(C)OC(N)=C(C#N)C1c1cc(C)c(OC(C)=O)c(C)c1]

Following the general method, 4-formyl-2,6-dimethylphenyl acetate (85 mg, 0.44 mmol), malononitrile (32 mg, 0.49 mmol), ethyl acetoacetate (63 mg, 0.49 mmol), piperidine (2 drops), and ethanol (3 mL), gave the title compound as a white solid (146 mg, 90%). $^1$H NMR (300 MHz, CDCl$_3$) δ 6.85 (s, 2H), 4.47 (bs, 2H), 4.37 (s, 1H), 4.19-3.94 (m, 2H), 2.37 (s, 3H), 2.31 (s, 3H), 2.11 (s, 6H), 1.12 (t, J=7.0 Hz, 3H). MS (ESI) m/z: 371.4 (M+H)$^+$ (55%); 740.8 (2M+H)$^+$ (100%).

(e) Ethyl 6-amino-5-cyano-2-methyl-4-(4-(pyridin-2-yl)phenyl)-4H-pyran-3-carboxylate (11p)

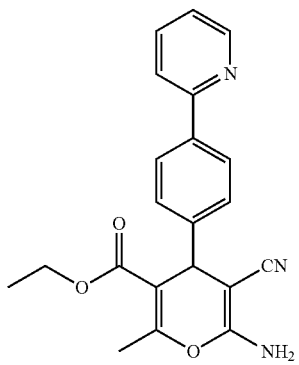 [SMILES: CCOC(=O)C1=C(C)OC(N)=C(C#N)C1c1ccc(-c2ccccn2)cc1]

Following the general method, 4-(2-pyridyl)benzaldehyde (250 mg, 1.36 mmol), malononitrile (99 mg, 1.50 mmol), ethyl acetoacetate (195 mg, 1.50 mmol), piperidine (3 drops), and ethanol (5 mL), gave the title compound as a white solid (410 mg, 83%). $^1$H NMR (300 MHz, CDCl$_3$) δ 8.71-8.64 (m, 1H), 7.93 (d, J=8.4 Hz, 2H), 7.79-7.67 (m, 2H), 7.31 (d, J=8.4 Hz, 2H), 7.22 (ddd, J=6.6, 4.8, 1.6 Hz, 1H), 4.52 (s, 1H), 4.47 (s, 2H), 4.03 (q, J=7.1 Hz, 2H), 2.40 (d, J=0.9 Hz, 3H), 1.11 (t, J=7.1 Hz, 3H). MS (ESI) m/z: 362.6 (M+H)$^+$ (100%).

(f) Ethyl 6-amino-5-cyano-2-methyl-4-(quinolin-2-yl)-4H-pyran-3-carboxylate (11s)

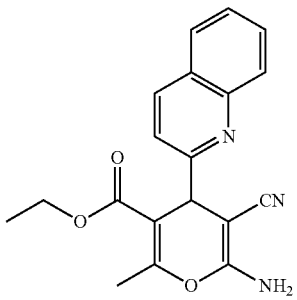 [SMILES: CCOC(=O)C1=C(C)OC(N)=C(C#N)C1c1ccc2ccccc2n1]

Following the general method, 2-quinoline carboxaldehyde (250 mg, 1.59 mmol), malononitrile (115 mg, 1.75 mmol), ethyl acetoacetate (228 mg, 1.75 mmol), piperidine (3 drops), and ethanol (5 mL), gave the title compound as a white solid after recrystallisation (302 mg, 57%). $^1$H NMR (300 MHz, DMSO) δ 8.32 (d, J=8.5 Hz, 1H), 7.98-7.90 (m, 2H), 7.73 (ddd, J=8.5, 6.9, 1.4 Hz, 1H), 7.56 (ddd, J=8.0, 6.9, 1.2 Hz, 1H), 7.40 (d, J=8.4 Hz, 1H), 6.98 (s, 2H), 4.63 (d, J=1.0 Hz, 1H), 3.89 (qd, J=7.1, 2.7 Hz, 2H), 2.38 (d, J=0.8 Hz, 3H), 0.88 (t, J=7.1 Hz, 3H). MS (ESI) m/z: 336.4 (M+H)$^+$ (100%).

(g) Ethyl 6-amino-5-cyano-2-methyl-4-(quinolin-3-yl)-4H-pyran-3-carboxylate (11t)

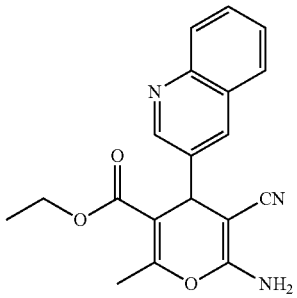 [SMILES: CCOC(=O)C1=C(C)OC(N)=C(C#N)C1c1cnc2ccccc2c1]

Following the general method, 3-quinoline carboxaldehyde (50 mg, 0.32 mmol), malononitrile (23 mg, 0.35 mmol), ethyl acetoacetate (45 mg, 0.35 mmol), piperidine (1 drop), and ethanol (3 mL), gave the title compound as a white solid (85 mg, 79%). $^1$H NMR (300 MHz, CDCl$_3$) δ 8.80 (s, 1H), 8.08 (d, J=8.4 Hz, 1H), 7.96 (s, 1H), 7.80 (d, J=8.2 Hz, 1H), 7.69 (t, J=7.6 Hz, 1H), 7.54 (t, J=7.5 Hz, 1H), 4.67 (s, 1H), 4.62 (bs, 2H), 4.03 (q, J=7.0 Hz, 2H), 2.43 (s, 3H), 1.11 (t, J=7.0 Hz, 3H). MS (ESI) m/z: 336.4 (M+H)$^+$ (100%).

(h) Ethyl 6-amino-5-cyano-2-methyl-4-(quinolin-4-yl)-4H-pyran-3-carboxylate (11u)

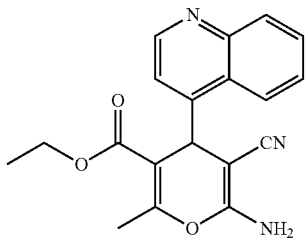 [SMILES: CCOC(=O)C1=C(C)OC(N)=C(C#N)C1c1ccnc2ccccc12]

Following the general method, 4-quinoline carboxaldehyde (250 mg, 1.59 mmol), malononitrile (115 mg, 1.75 mmol), ethyl acetoacetate (228 mg, 1.75 mmol), piperidine (2 drops), and ethanol (5 mL), gave the title compound as a white solid (395 mg, 74%). $^1$H NMR (300 MHz, CDCl$_3$) δ 8.86 (d, J=4.3 Hz, 1H), 8.31 (d, J=8.5 Hz, 1H), 8.12 (d, J=8.4 Hz, 1H), 7.73 (t, J=7.5 Hz, 1H), 7.62 (t, J=7.6 Hz, 1H), 7.20 (d, J=4.4 Hz, 1H), 5.38 (s, 1H), 4.60 (bs, 2H), 3.92-3.73 (m, 2H), 2.48 (s, 3H), 0.73 (t, J=7.1 Hz, 3H). MS (ESI) m/z: 336.2 (M+H)$^+$ (100%).

(i) 4-(2-Amino-3-cyano-5-(methoxycarbonyl)-6-methyl-4H-pyran-4-yl)benzoic Acid (13b)

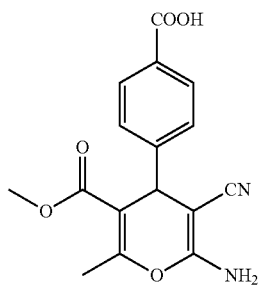 [SMILES: COC(=O)C1=C(C)OC(N)=C(C#N)C1c1ccc(C(=O)O)cc1]

Piperidine (2 drops) was added to a suspension of 4-(2,2-dicyanovinyl)benzoic acid (200 mg, 1.01 mmol) and methyl acetoacetate (117 mg, 1.01 mmol) in EtOH (3 mL). The mixture was stirred at ambient temperature for 6 h. The resulting precipitate was collected and washed with cold EtOH to give a white solid (117 mg). Column chromatography (SiO$_2$, EtOAc:MeOH, 9:1) afforded the title compound as white solid (78 mg, 25%). $^1$H NMR (400 MHz, MeOD) δ 7.96 (d, J=8.2 Hz, 2H), 7.29 (d, J=8.3 Hz, 2H), 4.46 (s, 1H), 3.57 (s, 3H), 2.39 (s, 3H). LCMS (ESI) m/z: 315.1 (M+H)$^+$ (100%).

(j) 4-(2-Amino-5-(benzyloxycarbonyl)-3-cyano-6-methyl-4H-pyran-4-yl)benzoic Acid (14b)

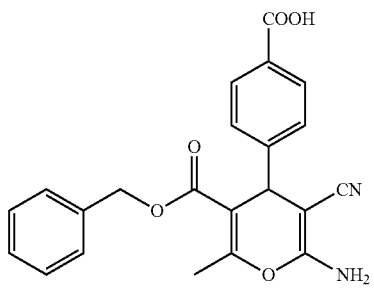 [SMILES: CC1=C(C(=O)OCc2ccccc2)C(c2ccc(C(=O)O)cc2)C(C#N)=C(N)O1]

(i) 4-(2,2-dicyanovinyl)benzoic Acid

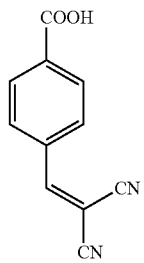 [SMILES: N#CC(C#N)=Cc1ccc(C(=O)O)cc1]

Piperidine (66 μL, 0.67 mmol) was added to a mixture of malononitrile (480 mg, 7.27 mmol) and 4-carboxybenzaldehyde (1.0 g, 6.65 mmol) in EtOH (5 mL). The suspension was heated to reflux for 18 h. After cooling the solvent was removed in vacuo and taken up in toluene. The resulting precipitate was collected and washed with toluene and cold EtOH to give the intermediate as a pale yellow solid (1.28 g, 85%). $^1$H NMR (400 MHz, MeOD) δ 8.29 (s, 1H), 8.17 (d, J=8.5 Hz, 2H), 8.04 (d, J=8.3 Hz, 2H).

(ii) 4-(2-amino-5-(benzyloxycarbonyl)-3-cyano-6-methyl-4H-pyran-4-yl)benzoic Acid Piperidine (5 μL, 0.05 mmol) was added to a suspension of 4-(2,2-dicyanovinyl)benzoic acid (100 mg, 0.5 mmol) and benzyl acetoacetate (87 μL, 0.5 mmol) in EtOH (3 mL). The mixture was stirred at ambient temperature for 6 h. The resulting precipitate was collected and washed with cold EtOH to give a white solid (55 mg). Column chromatography (SiO$_2$, EtOAc) afforded the title compound as beige solid (31 mg, 16%). $^1$H NMR (400 MHz, MeOD) δ 7.89 (d, J=8.4 Hz, 2H), 7.28-7.16 (m, 5H), 7.02 (dd, J=7.8, 1.7 Hz, 2H), 5.09 (d, J=12.3 Hz, 1H), 4.94 (d, J=12.3 Hz, 1H), 4.45 (d, J=0.9 Hz, 1H), 2.40 (d, J=1.0 Hz, 3H). $^{13}$C NMR (100 MHz, MeOD) δ 169.79, 167.03, 160.45, 159.62, 151.19, 137.07, 131.11, 130.73, 129.39, 129.22, 129.13, 128.63, 120.59, 108.00, 67.43, 58.77, 40.46, 18.71. MS (ESI) m/z: 391.4 (M+H)$^+$ (60%).

(k) Benzyl 6-amino-5-cyano-4-(4-cyanophenyl)-2-methyl-4H-pyran-3-carboxylate (14d)

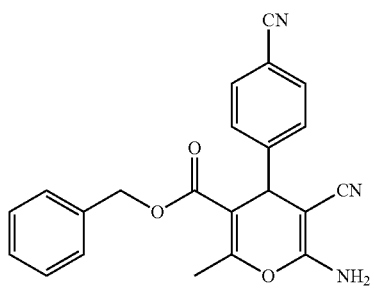 [SMILES: CC1=C(C(=O)OCc2ccccc2)C(c2ccc(C#N)cc2)C(C#N)=C(N)O1]

(i) 2-(4-cyanobenzylidene)malononitrile

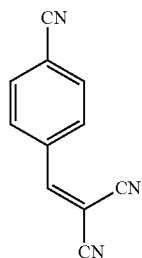

A suspension of malononitrile (111 mg, 1.68 mmol) and 4-cyanobenzaldehyde (200 mg, 1.53 mmol) in H$_2$O (10 mL) was stirred at 100° C. for 8 h. The resulting precipitate was collected and washed with H$_2$O to give the title compound as a cream solid (228 mg, 83%). $^1$H NMR (400 MHz, MeOD) δ 8.31 (s, 1H), 8.09 (d, J=8.3 Hz, 2H), 7.93 (d, J=8.5 Hz, 2H).

(ii) Benzyl 6-amino-5-cyano-4-(4-cyanophenyl)-2-methyl-4H-pyran-3-carboxylate Piperidine (3 µL, 0.028 mmol) was added to a suspension of the intermediate 2-(4-cyanobenzylidene)malononitrile (50 mg, 0.28 mmol) and benzyl acetoacetate (48 µL, 0.28 mmol) in EtOH (2 mL). The mixture was stirred at ambient temperature for 1 h. The resulting precipitate was collected and washed with cold EtOH to give the title compound as a white solid (77 mg, 74%). $^1$H NMR (400 MHz, CDCl$_3$) δ 7.51 (d, J=8.5 Hz, 2H), 7.35-7.26 (m, 3H), 7.21 (d, J=8.3 Hz, 2H), 7.06-7.01 (m, 2H), 5.08 (d, J=12.1 Hz, 1H), 4.93 (d, J=12.1 Hz, 1H), 4.54 (s, 2H), 4.49 (d, J=0.8 Hz, 1H), 2.42 (d, J=1.0 Hz, 3H). $^{13}$C NMR (100 MHz, CDCl$_3$) δ 165.23, 158.59, 157.62, 148.97, 135.13, 132.65, 128.67, 128.62, 128.46, 128.43, 118.86, 118.35, 111.18, 106.64, 66.92, 61.27, 39.06, 18.78.

(l) Benzyl 6-amino-5-cyano-4-(3-cyanophenyl)-2-methyl-4H-pyran-3-carboxylate (14e)

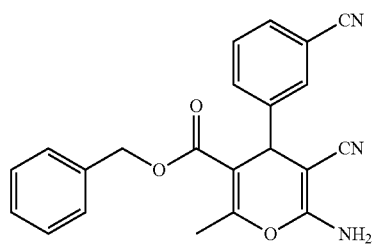 [SMILES: CC1=C(C(=O)OCc2ccccc2)C(c2cccc(C#N)c2)C(C#N)=C(N)O1]

(i) 2-(3-cyanobenzylidene)malononitrile

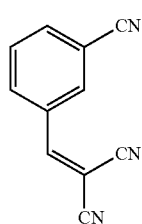 [SMILES: N#CC(C#N)=Cc1cccc(C#N)c1]

A suspension of malononitrile (111 mg, 1.68 mmol) and 3-formyl benzonitrile (200 mg, 1.53 mmol) in H$_2$O (5 mL) was stirred at 100° C. with microwave heating for 3 min. The resulting precipitate was collected and washed with H$_2$O to give the title compound as a white solid (225 mg, 82%). $^1$H NMR (400 MHz, CDCl$_3$) δ 8.20 (ddd, J=8.0, 1.2, 0.6 Hz, 1H), 8.08-8.07 (m, 1H), 7.90 (dt, J=7.8, 1.3 Hz, 1H), 7.79 (s, 1H), 7.71 (t, J=7.9 Hz, 1H). MS (ESI) m/z: 178.2 (M−H)$^-$ (50%).

(ii) benzyl 6-amino-5-cyano-4-(3-cyanophenyl)-2-methyl-4H-pyran-3-carboxylate Piperidine (3 µL, 0.028 mmol) was added to a suspension of 2-(3-cyanobenzylidene)malononitrile (50 mg, 0.28 mmol) and benzyl acetoacetate (48 µL, 0.28 mmol) in EtOH (2 mL). The mixture was stirred at ambient temperature for 1 h. The resulting precipitate was collected and washed with cold EtOH to give the title compound as a white solid (82 mg, 79%). $^1$H NMR (400 MHz, CDCl$_3$) δ 7.49 (dt, J=7.1, 1.6 Hz, 1H), 7.40-7.27 (m, 6H), 7.10-7.05 (m, 2H), 5.06 (d, J=12.1 Hz, 1H), 4.95 (d, J=12.1 Hz, 1H), 4.59 (bs, 2H), 4.46 (d, J=0.9 Hz, 1H), 2.42 (d, J=1.0 Hz, 3H). $^{13}$C NMR (100 MHz, CDCl$_3$) δ 165.23, 158.60, 157.70, 145.39, 135.07, 132.36, 131.31, 131.05, 129.55, 128.76, 128.68, 128.49, 118.83, 118.39, 112.84, 106.79, 67.04, 61.36, 38.70, 18.83.

(m) 4-(3-Acetyl-6-amino-5-cyano-2-methyl-4H-pyran-4-yl)benzoic Acid (15a)

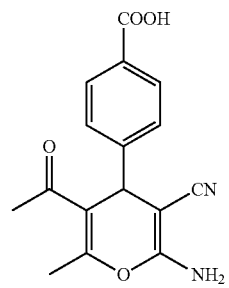 [SMILES: CC(=O)C1=C(C)OC(N)=C(C#N)C1c1ccc(C(=O)O)cc1]

Piperidine (38 µL, 0.38 mmol) was added to a suspension of 4-(2,2-dicyanovinyl)benzoic acid (750 mg, 3.78 mmol) and acetyl acetone (379 mg, 3.78 mmol) in EtOH (5 mL). The mixture was stirred at ambient temperature for 18 h. The resulting precipitate was collected and washed with cold EtOH to give the title compound as a white solid (840 mg, 75%). $^1$H NMR (400 MHz, MeOD) δ 7.99 (d, J=8.4 Hz, 2H), 7.32 (d, J=8.3 Hz, 2H), 4.57 (d, J=0.8 Hz, 1H), 2.33 (d, J=0.9 Hz, 1H), 2.10 (s, 2H). MS (ESI) m/z: 297.3 (M−H)$^-$ (40%).

A sample was dissolved in an aqueous solution of NH$_4$HCO$_3$ (2 eq.) and lyophilized. $^1$H NMR (400 MHz, D$_2$O) δ 7.90 (d, J=8.4 Hz, 2H), 7.38 (d, J=8.3 Hz, 2H), 4.63 (d, J=0.8 Hz, 1H), 2.32 (d, J=0.9 Hz, 3H), 2.20 (s, 3H).

(n) 3-(3-Acetyl-6-amino-5-cyano-2-methyl-4H-pyran-4-yl)benzoic Acid (15b)

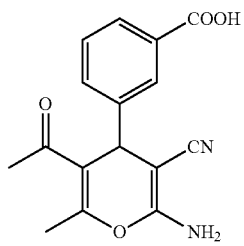 [SMILES: CC(=O)C1=C(C)OC(N)=C(C#N)C1c1cccc(C(=O)O)c1]

Piperidine (2 drops) was added to a solution of malononitrile (48 mg, 0.73 mmol) and 3-carboxybenzaldehyde (100 mg, 0.66 mmol) in acetonitrile (3 mL) and stirred at ambient temperature for 1 h. Acetyl acetone (75 μL, 0.73 mmol) was added and the mixture stirred at ambient temperature for 4 h. The volume of solvent was reduced and the resulting residue purified by column chromatography (SiO$_2$, CHCl$_3$:ACN:AcOH, 9:0.7:0.3). The product was obtained as a beige solid (13 mg, 7%). $^1$H NMR (400 MHz, MeOD) δ 7.92-7.90 (m, 1H), 7.86 (m, 1H), 7.47-7.44 (m, 2H), 4.57 (d, J=0.9 Hz, 1H), 2.33 (d, J=0.9 Hz, 3H), 2.10 (s, 3H).

(o) 5-Acetyl-2-amino-6-methyl-4-(quinolin-2-yl)-4H-pyran-3-carbonitrile (15i)

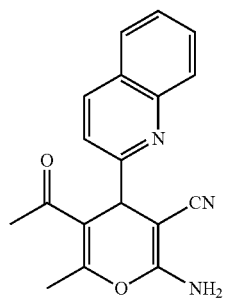 [SMILES: CC(=O)C1=C(C)OC(N)=C(C#N)C1c1ccc2ccccc2n1]

(i) 2-(quinolin-2-ylmethylene)malononitrile

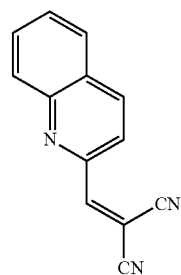 [SMILES: N#CC(C#N)=Cc1ccc2ccccc2n1]

A suspension of malononitrile (92 mg, 1.39 mmol) and 2-quinoline carboxaldehyde (200 mg, 1.27 mmol) in H$_2$O (5 mL) were stirred at ambient temperature for 7 h. The precipitate was collected and washed with H$_2$O to give the title compound as a green solid (240 mg, 92%). $^1$H NMR (400 MHz, MeOD) δ 8.48 (d, J=8.0 Hz, 1H), 8.37 (s, 1H), 8.16 (d, J=8.6 Hz, 1H), 8.00 (d, J=8.2 Hz, 1H), 7.86 (ddd, J=8.5, 6.9, 1.4 Hz, 1H), 7.80 (d, J=8.4 Hz, 1H), 7.73 (ddd, J=8.1, 6.9, 1.2 Hz, 1H).

(ii) 5-acetyl-2-amino-6-methyl-4-(quinolin-2-yl)-4H-pyran-3-carbonitrile

Piperidine (2.4 μL, 0.024 mmol) was added to a solution of 2-(quinolin-2-ylmethylene)malononitrile (50 mg, 0.24 mmol) and acetyl acetone (25 μL, 0.24 mmol) in EtOH (0.5 mL). The mixture was stirred at ambient temperature for 6 h. The resulting precipitate was collected and washed with cold EtOH to give a pale brown solid (24 mg, 33%). $^1$H NMR (400 MHz, MeOD) δ 8.33 (d, J=8.5 Hz, 1H), 8.03 (d, J=8.5 Hz, 1H), 7.90 (dd, J=8.2, 1.2 Hz, 1H), 7.76 (ddd, J=8.5, 6.9, 1.5 Hz, 1H), 7.59 (ddd, J=8.1, 6.9, 1.2 Hz, 1H), 7.44 (d, J=8.5 Hz, 1H), 4.83 (d, J=1.0 Hz, 1H), 2.36 (d, J=1.0 Hz, 3H), 2.16 (d, J=3.4 Hz, 3H). MS (ESI) m/z: 306.5 (M+H)$^+$ (100%).

(p) 5-Acetyl-2-amino-4-(3-cyanophenyl)-6-methyl-4H-pyran-3-carbonitrile (15e)

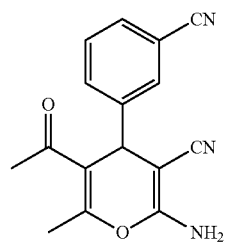 [SMILES: CC(=O)C1=C(C)OC(N)=C(C#N)C1c1cccc(C#N)c1]

Piperidine (3 μL, 0.028 mmol) was added to a suspension of 2-(3-cyanobenzylidene)malononitrile (50 mg, 0.28 mmol) and acetyl acetone (28 mg, 0.28 mmol) in EtOH (2 mL). The mixture was stirred at ambient temperature for 1 h. The resulting precipitate was collected and washed with cold EtOH to give a white solid (64 mg). Column chromatography (SiO$_2$, EtOAc:Hexane, 1:2 followed by 100% EtOH) afforded the title compound as white solid (36 mg, 46%). $^1$H NMR (400 MHz, DMSO) δ 7.72 (dt, J=7.3, 1.6 Hz, 1H), 7.64 (s, 1H), 7.57 (t, J=7.5 Hz, 1H), 7.53 (dt, J=7.9, 1.6 Hz, 1H), 6.99 (bs, 2H), 4.57 (s, 1H), 2.27 (d, J=0.7 Hz, 3H), 2.09 (s, 3H). $^{13}$C NMR (100 MHz, DMSO) δ 197.93, 158.45, 156.07, 146.31, 132.25, 130.92, 130.61, 130.11, 119.53, 118.72, 114.32, 111.62, 56.88, 38.29, 30.12, 18.77.

(q) 5-Acetyl-2-amino-6-methyl-4-(4-(thiophen-2-yl)phenyl)-4H-pyran-3-carbonitrile (15 g)

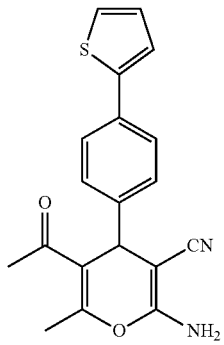 [SMILES: CC(=O)C1=C(C)OC(N)=C(C#N)C1c1ccc(-c2cccs2)cc1]

(i) 2-(4-(thiophen-2-yl)benzylidene)malononitrile

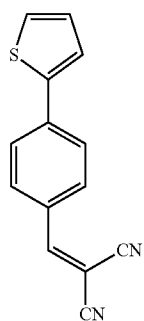

Piperidine (2.6 µL, 0.027 mmol) was added to a solution of malononitrile (19 mg, 0.29 mmol) and 4-(2-thienyl)benzaldehyde (50 mg, 0.27 mmol) in EtOH (1.5 mL). The mixture was stirred at ambient temperature for 1 h. The resulting precipitate was collected and washed with cold EtOH to give the intermediate as a yellow solid (53 mg, 83%). $^1$H NMR (400 MHz, CDCl$_3$) δ 7.93 (d, J=8.4 Hz, 2H), 7.76 (d, J=8.5 Hz, 2H), 7.72 (s, 1H), 7.51 (dd, J=3.7, 1.1 Hz, 1H), 7.44 (dd, J=5.1, 1.1 Hz, 1H), 7.15 (dd, J=5.1, 3.7 Hz, 1H).

(ii) 5-acetyl-2-amino-6-methyl-4-(4-(thiophen-2-yl)phenyl)-4H-pyran-3-carbonitrile Piperidine (2.2 µL, 0.022 mmol) was added to a suspension of the intermediate (SJM-4-148) (53 mg, 0.22 mmol) and acetyl acetone (23 µL, 0.22 mmol) in toluene (1 mL). The mixture was stirred at ambient temperature for 4 h. The resulting precipitate was collected and washed with toluene to give a pale yellow solid. Column chromatography (SiO$_2$, CH$_2$Cl$_2$:Et$_2$O, 95:5) afforded the title compound as a white solid (40 mg, 77%). HRMS (ESI$^+$): Found: m/z 337.1008 (M+H)$^+$, C$_{19}$H$_{17}$N$_2$O$_2$S requires m/z 337.1001. $^1$H NMR (400 MHz, CDCl$_3$) δ 7.58 (d, J=8.3 Hz, 2H), 7.30-7.25 (m, 2H), 7.21 (d, J=8.3 Hz, 2H), 7.07 (dd, J=5.1, 3.6 Hz, 1H), 4.46 (s, 1H), 4.43 (bs, 2H), 2.32 (d, J=1.0 Hz, 3H), 2.09 (s, 3H).

(r) 5-Acetyl-2-amino-6-methyl-4-(quinoxalin-6-yl)-4H-pyran-3-carbonitrile (15j)

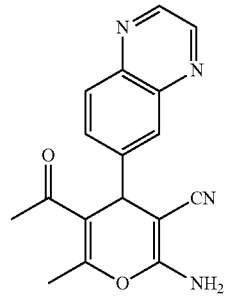 [SMILES: CC(=O)C1=C(C)OC(N)=C(C#N)C1c1ccc2nccnc2c1]

(i) 2-(quinoxalin-6-ylmethylene)malononitrile

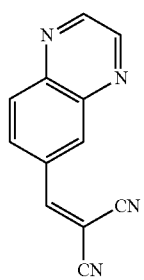 [SMILES: N#CC(C#N)=Cc1ccc2nccnc2c1]

Piperidine (4.7 µL, 0.047 mmol) was added to a solution of malononitrile (34 mg, 0.52 mmol) and quinoxaline-6-carbaldehyde (75 mg, 0.47 mmol) in EtOH (1 mL). The mixture was stirred at ambient temperature for 1 h. The resulting precipitate was collected and washed with cold EtOH to give the intermediate as a light brown solid (66 mg, 68%). $^1$H NMR (400 MHz, CDCl$_3$) δ 8.97 (s, 2H), 8.55 (d, J=2.1 Hz, 1H), 8.37 (dd, J=8.9, 2.1 Hz, 1H), 8.27 (d, J=8.9 Hz, 1H), 8.01 (s, 1H).

(ii) 5-acetyl-2-amino-6-methyl-4-(quinoxalin-6-yl)-4H-pyran-3-carbonitrile

Piperidine (1.4 µL, 0.015 mmol) was added to a suspension of the intermediate (SJM-4-152) (30 mg, 0.145 mmol) and acetyl acetone (15 µL, 0.145 mmol) in toluene (1 mL). The mixture was stirred at ambient temperature for 4 h. The resulting precipitate was collected and washed with cold Et$_2$O to give the title compound as a beige solid (38 mg, 86%). HRMS (ESI$^+$): Found: m/z 307.1190 (M+H)$^+$, C$_{17}$H$_{15}$N$_4$O$_2$ requires m/z 307.1195. $^1$H NMR (400 MHz, CDCl$_3$) δ 8.86-8.81 (m, 2H), 8.11 (d, J=8.7 Hz, 1H), 7.92 (d, J=2.0 Hz, 1H), 7.69 (dd, J=8.7, 2.1 Hz, 1H), 4.72 (s, 1H), 4.59 (bs, 2H), 2.36 (d, J=0.9 Hz, 3H), 2.13 (s, 3H). $^{13}$C NMR (101 MHz, CDCl$_3$) δ 197.92, 157.70, 156.10, 145.54, 145.35, 145.26, 143.25, 142.63, 130.77, 129.91, 127.65, 118.58, 114.92, 61.83, 39.73, 30.17, 19.11.

(s) 2-(3-Acetyl-6-amino-5-cyano-2-methyl-4H-pyran-4-yl)benzoic Acid (15k)

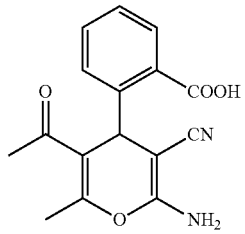 [SMILES: CC(=O)C1=C(C)OC(N)=C(C#N)C1c1ccccc1C(=O)O]

(i) 2-(2,2-dicyanovinyl)benzoic Acid

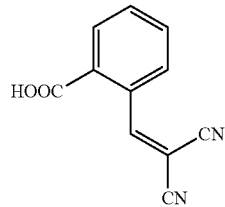 [SMILES: N#CC(C#N)=Cc1ccccc1C(=O)O]

A suspension of malononitrile (48 mg, 0.73 mmol) and 2-carboxybenzaldehyde (100 mg, 0.67 mmol) in $H_2O$ (4 mL) was stirred at 100° C. with microwave heating for 3 min. The resulting precipitate was collected and washed with $H_2O$ to give the title compound as a white solid (34 mg, 55%). $^1$H NMR (400 MHz, MeOD) δ 8.87 (s, 1H), 8.19 (dd, J=7.6, 1.2 Hz, 1H), 7.83-7.78 (m, 1H), 7.75 (td, J=7.5, 1.4 Hz, 1H), 7.70 (td, J=7.5, 1.3 Hz, 1H).

(ii) 2-(3-acetyl-6-amino-5-cyano-2-methyl-4H-pyran-4-yl)benzoic Acid

Piperidine (12.5 μL, 0.125 mmol) was added to a suspension of 2-(2,2-dicyanovinyl)benzoic acid (50 mg, 0.25 mmol) and acetyl acetone (25 mg, 0.25 mmol) in EtOH (3 mL). The mixture was stirred for 3 d. The solvent was removed in vacuo and the residue taken up in EtOAc and stirred for 18 h. The resulting precipitate was collected and washed with cold EtOAc to give a pale yellow solid (76 mg). Column chromatography ($SiO_2$, ACN:$CHCl_3$, 2:1, followed by EtOAc:MeOH, 95:5) gave a yellow residue (33 mg). $^1$H NMR (400 MHz, MeOD) δ 7.94 (dd, J=7.9, 1.2 Hz, 1H), 7.52 (td, J=7.6, 1.4 Hz, 1H), 7.31 (td, J=7.7, 1.3 Hz, 1H), 7.26 (dd, J=7.9, 1.0 Hz, 1H), 6.02 (d, J=1.0 Hz, 1H), 2.29 (d, J=1.0 Hz, 3H), 2.05 (s, 3H).

(t) 4-(2-Acetamido-5-acetyl-3-cyano-6-methyl-4H-pyran-4-yl)benzoic Acid (16)

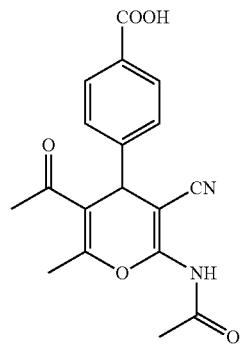 [SMILES: CC(=O)NC1=C(C#N)C(c2ccc(C(=O)O)cc2)C(C(C)=O)=C(C)O1]

A solution of 4-(3-acetyl-6-amino-5-cyano-2-methyl-4H-pyran-4-yl)benzoic acid (15a) (250 mg, 0.84 mmol) in acetic anhydride (3 mL) was heated to reflux for 3 h. The mixture was concentrated under a stream of $N_2$ and then poured into ice cold $H_2O$. The aqueous solution was extracted with EtOAc (3×20 mL) and the combined organic extract was washed with brine (20 mL), dried ($MgSO_4$), filtered and reduced in vacuo to give a yellow oil. The yellow oil was dissolved in EtOH (5 mL) and hydrazine hydrate (1.3 eq.) was added. After stirring for 30 min the suspension was reduced in vacuo and taken up in $H_2O$ (10 mL) and extracted with EtOAc (3×10 mL). The combined organic extract was dried ($MgSO_4$), filtered and solvent removed in vacuo to give a yellow oil. Column chromatography ($SiO_2$, EtOAc: MeOH, 95:5 followed by 100% EtOH) afforded the title compound (20 mg, 7%). $^1$H NMR (400 MHz, MeOD) δ 8.02 (d, J=8.4 Hz, 2H), 7.41 (d, J=8.3 Hz, 2H), 4.80 (s, 1H), 2.34 (d, J=0.8 Hz, 3H), 2.15 (s, 3H), 2.08 (s, 3H). MS (ESI) m/z: 341.4 (M+H)$^+$ (100%).

(u) 4-(2-Amino-3,5-bis(ethoxycarbonyl)-6-methyl-4H-pyran-4-yl)benzoic Acid (17a)

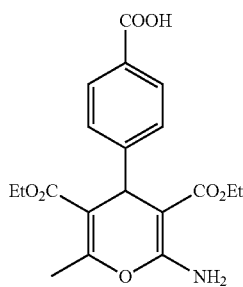 [SMILES: CCOC(=O)C1=C(C)OC(N)=C(C(=O)OCC)C1c1ccc(C(=O)O)cc1]

(i) (Z)-4-(2-cyano-3-ethoxy-3-oxoprop-1-enyl)benzoic Acid

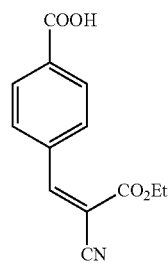 [SMILES: CCOC(=O)/C(C#N)=C\c1ccc(C(=O)O)cc1]

Piperidine (13 µL, 0.13 mmol) was added to a suspension of ethyl cyanoacetate (151 mg, 1.33 mmol) and 4-carboxybenzaldehyde (200 mg, 1.33 mmol) in EtOH (3 mL). The mixture was heated to reflux for 3 h. The mixture was concentrated in vacuo. Toluene was added and the resulting precipitate was collected and washed with toluene to give the intermediate as a white solid (278 mg, 85%). $^1$H NMR (400 MHz, MeOD) δ 8.40 (s, 1H), 8.16 (d, J=8.6 Hz, 2H), 8.10 (d, J=8.4 Hz, 2H), 4.39 (q, J=7.1 Hz, 2H), 1.39 (t, J=7.1 Hz, 3H).

(ii) 4-(2-amino-3,5-bis(ethoxycarbonyl)-6-methyl-4H-pyran-4-yl)benzoic Acid

Piperidine (20 µL, 0.2 mmol) was added to a suspension of (Z)-4-(2-cyano-3-ethoxy-3-oxoprop-1-enyl)benzoic acid (50 mg, 0.2 mmol) and ethyl acetoacetate (26 mg, 0.2 mmol) in EtOH (3 mL). The mixture was stirred at ambient temperature for 2 d. Piperidine (10 µL, 0.1 mmol) was added and solution stirred for a further 1 d. The mixture was concentrated in vacuo and the residue purified by column chromatography (SiO2, EtOAc:Hexane, 2:1) to give a yellow oil. Recystallisation from EtOH gave a white solid (>5 mg). $^1$H NMR (400 MHz, MeOD) δ 7.88 (d, J=8.4 Hz, 2H), 7.29 (d, J=8.3 Hz, 2H), 4.73 (d, J=0.7 Hz, 1H), 4.12-3.98 (m, 4H), 2.37 (d, J=0.8 Hz, 3H), 1.18 (t, J=7.1 Hz, 3H), 1.14 (t, J=7.1 Hz, 3H). MS (ESI) m/z: 372.1 (M+H)$^+$ (100%).

(v) 4-(3-Acetyl-6-amino-5-(ethoxycarbonyl)-2-methyl-4H-pyran-4-yl)benzoic Acid (17b)

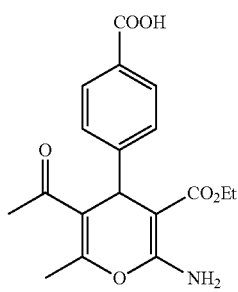 [SMILES: CCOC(=O)C1=C(N)OC(C)=C(C(C)=O)C1c1ccc(C(=O)O)cc1]

Piperidine (30 µL, 0.3 mmol) was added to a suspension of (Z)-4-(2-cyano-3-ethoxy-3-oxoprop-1-enyl)benzoic acid (50 mg, 0.2 mmol) and acetyl acetone (20 mg, 0.2 mmol) in EtOH (3 mL). The mixture was stirred at ambient temperature for 24 h. Analytical HPLC shows a 1:1 ratio of starting material to product however further reaction time leads to decomposition. Purification by column chromatography (SiO$_2$, EtOAc) afforded the title compound (2 mg, 3%). $^1$H NMR (400 MHz, MeOD) δ 7.90 (d, J=8.4 Hz, 2H), 7.31 (d, J=8.3 Hz, 2H), 4.79 (s, 1H), 4.13-4.02 (m, 2H), 2.32 (d, J=0.7 Hz, 3H), 2.18 (s, 3H), 1.20 (t, J=7.1 Hz, 3H).

Example 2

An in vitro enzymatic assay was used to initially assess IRAP inhibitory activity.
IRAP Enzymatic Assay
Crude membranes were prepared from HEK 293T cells transfected with IRAP or empty vector, then solubilized in buffer consisting of 50 mM Tris-HCl, 1% Triton X-100, pH 7.4 at 4° C. under agitation over 5 h. After solubilization, the membranes were pelleted by centrifugation at 23,100 g for 15 min at 4° C., and the supernatant was reserved as the source of IRAP activity. The enzymatic activities of recombinant IRAP were determined by the hydrolysis of the synthetic substrate Leu-MCA (Sigma-Aldrich, Missouri, USA) monitored by the release of a fluorogenic product, MCA, at excitation and emission wavelengths of 380 and 440 nm, respectively. Assays were performed in 96-well plates; each well contains between 0.2-10 µg solubilized membrane protein, a range of concentration of substrate in a final volume of 100 µL 50 mM Tris-HCl buffer (pH 7.4). Non-specific hydrolysis of the substrate was corrected by subtracting the emission from incubations with membranes transfected with empty vector. Reactions proceeded at 37° C. for 30 min within a thermostatted FLEX station fluorescence microplate reader (Molecular Devices, Sunnyvale, Calif.). The kinetic parameters ($K_m$ and V) were determined by non-linear fitting of the Michaelis-Menten equation (GraphPad Prism, GraphPad Software Inc., CA, USA); final concentrations of Leu-MCA of 15.6 µM-1 mM. Inhibitor constants ($K_i$) for the competitive inhibitors were calculated from the relationship IC$_{50}$=(1+[S]/K$_m$), where IC$_{50}$ values were determined over a range of inhibitor concentrations ($10^{-9}$ to $10^{-4}$ M). $K_m$ values of IRAP for Leu-MCA were determined from the kinetic studies. Binding affinities of the compounds to IRAP were examined by monitoring the inhibition of the hydrolysis of Leu-MCA in the presence of increasing concentrations of the compounds ($10^{-8}$ to $10^{-3}$ M). All data obtained were from at least three separate experiments performed in duplicate.

The results for some compounds of Formula (I) are set out below in Tables 2-1 to 2-8. The compounds were obtained commercially (Specs, Interbioscreen Ltd and Chembridge Corporation) or prepared according to the procedures outlined above.

TABLE 2-1

11

| Compound | Ar | $K_i$ (µM) | IC50 (µM) |
|---|---|---|---|
| 11a | 3-bromo-4-hydroxy-5-methoxyphenyl | 13.7 | 23 |
| 11b | 3-methoxy-4-hydroxyphenyl | 13.1 | 22 |
| 11c | 3-methoxyphenyl | | |
| 11d | 3-bromophenyl | | |
| 11e | 4-hydroxyphenyl | 61.3 | 103 |
| 11f | 3-bomo-4-methoxyphenyl | | |
| 11g | 3,4-methylenedioxyphenyl | | >50 |
| 11h | 3,4-methylenedioxy-5-methoxyphenyl | 37.5 | 63 |
| 11i | 3,4-dimethoxyphenyl | | >50 |
| 11j | 4-cyanophenyl | | >100 |
| 11k | 4-carboxyphenyl | 18.4 | 31 |
| 11l | 4-nitrophenyl | | >100 |
| 11m | 3-carboxyphenyl | | >100 |
| 11n | 3-methyl-4-acetoxyphenyl | | >100 |
| 11o | 3,5-dimethoxy-4-acetoxyphenyl | | >100 |
| 11p | 4-(pyrid-2-yl)-phenyl | | >100 |
| 11q | pyridin-3-yl | | >50 |
| 11r | pyridin-4-yl | | >100 |
| 11s | quinolin-2-yl | | 3-40 |
| 11t | quinolin-3-yl | | >100 |
| 11u | quinolin-4-yl | | >100 |

TABLE 2-2

12

[Structure: 4-hydroxyphenyl (with R2' substituent) attached to a 4H-pyran ring bearing EtO2C, CN, R3, NH2, O]

| Compound | R3 | R2' | $K_i$ (μM) | IC50 (μM) |
|---|---|---|---|---|
| 12a | Et | OCH3 | 85.1 | 143 |
| 12b | Pr | OCH3 | | |
| 12c | Et | OEt | 67.2 | 113 |

TABLE 2-3

13

[Structure: Ar-substituted 4H-pyran with MeO2C, CN, H3C, NH2, O]

| Compound | Ar | $K_i$ (μM) | IC50 (μM) |
|---|---|---|---|
| 13a | 3,4-dimethoxyphenyl | | |
| 13b | 4-carboxyphenyl | 8.3 | 14 |
| 13c | 4-hydroxyphenyl | | >100 |
| 13d | 3-methoxy-4-hydroxyphenyl | 8.3 | 14 |

TABLE 2-4

14

[Structure: Ar-substituted 4H-pyran with BnO2C, CN, H3C, NH2, O]

| Compound | Ar | $K_i$ (μM) | IC50 (μM) |
|---|---|---|---|
| 14a | 3,4-dimethoxyphenyl | 16.7 | 28 |
| 14b | 4-carboxyphenyl | 3.0 | 5 |
| 14c | 4-methoxycarbonylphenyl | | 10-100 |
| 14d | 4-cyanophneyl | | >100 |
| 14e | 3-cyanophneyl | | — |

TABLE 2-5

15

[Structure: Ar-substituted 4H-pyran with acetyl (O=C-CH3), CN, H3C, NH2, O]

| Compound | Ar | $K_i$ (μM) | IC50 (μM) |
|---|---|---|---|
| 15a | 4-carboxyphenyl | 1.8 | 2-4 |
| 15b | 3-carboxyphenyl | 3.9 | 6-7 |
| 15c | 3-methoxy-4-hydroxyphenyl | 16.7 | 28 |

TABLE 2-5-continued

15

| Compound | Ar | $K_i$ (μM) | IC50 (μM) |
|---|---|---|---|
| 15d | 4-cyanophenyl | 59.5 | 100 |
| 15e | 3-cyanophenyl | | |
| 15f | 4-methoxycarbonylphenyl | | |
| 15g | 4-(thiophen-2-yl)phenyl | | |
| 15h | pyridin-3-yl | | |
| 15i | quinolin-2-yl | 10.1 | 17 |
| 15j | quinoxalin-6-yl | | >100 |
| 15k | 2-carboxyphenyl | | |

TABLE 2-6

16

[Structure: 4-carboxyphenyl substituted 4H-pyran with Ac, CN, H3C, NHAc, O]

| Compound | $K_i$ (μM) | IC50 (M) |
|---|---|---|
| 16 | 4.2 | 7 |

TABLE 2-7

17

[Structure: 4-carboxyphenyl substituted 4H-pyran with R2, CO2Et, H3C, NH2, O]

| Compound | R2 | $K_i$ (μM) | IC50 (μM) |
|---|---|---|---|
| 17a | CO2Et | 4.2 | 7 |
| 17b | Ac | | |

TABLE 2-8

| Compound | Ki (μ(M)) | IC50 μ(M) |
|---|---|---|
| 18 | | 40 |

Structure 18: 4-(3-bromo-4-hydroxy-5-methoxyphenyl)-3-cyano-... pyran compound

Example 3

The effects of Test Compound 1 (ammonium salt of 15a) on a cellular correlate of memory-dendritic spine densities

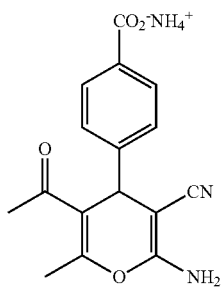

Chemical Formula: $C_{16}H_{17}N_3O_4$
Exact Mass: 315.12
Molecular Weight: 315.32
m/z: 315.12 (100.0%), 316.13 (17.7%), 317.13 (2.3%), 316.12 (1.1%)
Elemental Analysis: C, 60.94; H, 5.43; N, 13.33; O, 20.30

In Vitro Hippocampal Spine Density

Dendritic spines are a complex, distinct cellular compartment that protrude from neuronal processes, and act as a source of synaptic contact vital for plasticity, signalling and neuronal integration. Hippocampal spine density increases in the rat brain after learning of an associative task, thereby acting as a substrate for the new memories. Drugs that enhance actin reorganisation in dendritic spines, a requirement for stabilisation of memory, have been proposed for the treatment of memory disorders.

Hippocampi from E18 rat pups were dissected into cold Hank's Basic Salt Solution, rinsed three times and incubated in 5 ml of 0.12% w/v trypsin and 40 μg/ml DNAse (Sigma-Aldrich, St. Louis, USA) for 20 minutes at 37° C. Clumped cells were triturated for one minute with a sterile 1 ml pipette. The trypsin was de-activated by the addition of five ml of Dulbecco's modified Eagle Medium (DMEM) containing 10% foetal calf serum (DMEM-10), and the suspension then centrifuged at 180 g for five minutes. The supernatant was carefully removed and the pellet resuspended in 10 ml of DMEM-10 and the suspension again triturated for one minute. The suspension was re-centrifuged at the same speed and the pellet resuspended in 10 ml of DMEM-10. Cell density in a 1/10 dilution was measured using a haemocytometer. A suspension of $1.5 \times 10^5$ cells per ml was prepared in DMEM-10, containing 100 U/ml penicillin and 100 μg/ml streptomycin. Neurons were seeded onto poly-L-lysine coated glass coverslips in Nunc 24 well plates (Thermo Fisher Scientific, Waltham, USA). The media was changed to Neurobasal media with N2 and B27 supplements after two to four hours. Neurons were maintained in a 37° C. humidified incubator kept at 5% v/v $CO_2$, with half media changes twice weekly as required. Plates were used from 14 days in vitro.

The effect of Test Compound 1 on hippocampal spine density was tested. Examination of the effect of multiple applications of Test Compound 1 throughout the final week of culture. Test Compound 1 at 0.1 and 10 μM was applied on days 14, 17 and 20. DMSO vehicle controls were included in all experiments. At the completion of treatment on day 21, coverslips were washed and fixed with 4% PFA/0.12 M sucrose in PBS, and then stored at 4° C. in PBS containing 0.01% sodium azide until use.

For immunohistochemical staining of spines, coverslips were removed from plates and washed in PBS, then incubated in PBSX for 15 minutes to permeabilise membranes. Non-specific binding was blocked with 5% normal goat serum in PBSX for 30 minutes. Primary antibodies used were mouse anti-drebrin 1:500 (Stressegen, Ann Arbor, USA) for spines and rabbit anti-βIII-tubulin 1:1000 (clone Tuj1, Abcam) for all neuronal processes. These were applied simultaneously in blocking buffer for 90 minutes at room temperature. Coverslips were washed three times for five minutes each with PBS and then incubated in 1:500 goat anti-mouse Alexa 568 and 1:1000 goat anti-rabbit Alexa 488 for 45 minutes. After a five minute wash in PBS, coverslips were incubated in 1 nM Hoechst 33342 for 30 seconds, followed by two five minute washes in PBS. Coverslips were mounted with Aquamount (Thermo Fisher Scientific) onto SuperFrost® (Menzel-Glaser, Braunschweig, Germany) slides. Images were acquired at 630× magnification using an AxioVert 200 inverted microscope controlled by AxioVision® software. Spines highlighted by drebrin immunostaining were counted in Image J. Single neurites were identified and all spines along a fifty micron segment were counted. Eight to ten neurites from distinct neurons were identified per treatment. Counting was performed prior to decoding of treatment regime.

The results are depicted in FIG. 1. In primary cultures of rat hippocampal neurons, chronic treatment (3 doses of $10^{-5}$M) with Test Compound 1 resulted in statistically significant increases in dendritic spine densities.

Example 4

The effects of Test Compounds on performance in different memory tasks in vivo are demonstrated according to the following protocols.

Surgical Preparation of Rats

Male Sprague Dawley rats, (250-270 g) are housed individually and given water and standard rat chow ad libitum. On the day of surgery, the rats are anaesthetized with 5% isofluorane, placed in a stereotaxic frame and maintained on 2% isofluorane for the duration of the cannula implantation procedure. The rats are stereotaxically implanted with chronic indwelling cannula (Plastics One) into the cerebral lateral ventricles using the following flat skull coordinates 0.8 mm posterior to Bregma, 1.55 mm lateral to midline and 3.5 mm ventral to the dura. The cannula is then secured to the skull with stainless steel screws and dental cement. Seven days following surgery, proper cannula placement is verified by a bolus injection of angiotensin II (1 nmol/µl). Lack of a robust dipsogenic response within 5 min of angiotensin II administration would suggest misplacement of the cannula and the animal is then excluded from further studies.

Novel Object Recognition Task (Bevins et al, 2006)

The rats are allowed at least 5 days post-operative recovery prior to use in any behavioural paradigms. On the day of the acquisition trial, the rats are habituated for 5 min in the testing box (made from grey perspex of dimensions 60 cm width×60 cm length×50 cm height) in diffuse dim light and then returned to their home cage. The animals are then rested for at least 2 h and then injected with Test Compound in 2 µl of 10% dimethyl sulfoxide (DMSO). Control animals receive 2 µl of 10% DMSO. Following drug administration, the rats are returned to their home cage for 5 min and then placed in the testing box facing the opposite direction to 2 identical objects that have been secured to the floor in adjacent corners of the box. The rats are allowed 5 min to explore the objects (the definition of explore is that the animal's nose is less than 2 cm from object when it is facing the object). Animals that display a lack of interest in the object, exploration time of less than 15 secs are excluded from the study at this stage. The animals are then returned to their home cage during the intertrial interval of 20 h. On day 2 of testing, one of the objects is replaced by a novel object made from the same material but of a different shape—the rats are given 2 mins in the box. The recognition index is determined as the time spent exploring the novel object minus the time spent on the familiar object divided by the time spent on both objects.

Spontaneous Alternation Plus Maze (McNay et al, 2000)

The plus maze is composed of four arms with each arm measuring 75×10×20 cm. The floor and walls of the central platform and the floors of the arms are made of black plastic. The rats are injected with the Test Compound into the cerebral lateral ventricles 5 mins prior to being placed into the plus maze. Spontaneous alternation testing is conducted by placing the rat on the centre platform of the maze and allowing 20 min of unimpeded exploration. The number and sequence of arm entries are recorded for calculation of a percent alternation score. An alternation consists of 4 different arm choices of 5 consecutive arm entries. A ⅘ alternation score is computed by dividing the number of observed alternations in overlapping quintuplets by the number of possible alternations and multiplying the quotient by 100.

Elevated Plus Maze

The elevated plus maze is used to investigate the potential effect of IRAP inhibitors on stress or anxiety. The elevated plus maze consists of two open arms (70×10 cm) with a 5 cm high surrounding wall and two enclosed arms (70×10 cm) with a 27 cm high surrounding wall. The floors of the open and closed arms are white laminate, the open arm walls are clear perspex, and the closed arms walls dark grey perspex. The maze is elevated 85 cm above the ground in the centre of a room that is lit by overhead lights generating 124 lux. Naive rats, treated with Test Compounds dissolved in 10% DMSO or vehicle, will be placed 5 min after the icy injection, on the central platform facing one of the closed arms and behaviour monitored for 10 min. The time spent in the closed arms compared to the open arms is a measure of the anxiety status of the animals.

Locomotor Cell Activity

Locomotor activity of rats treated with 1 nmol Test Compounds intracerebrocentrically is monitored in special cages measuring 40×40×40 cm (Coulbourn Instruments, Philadelphia, USA) equipped with harmless infrared photobeams. Activity is measured when pairs of photobeams spaced 2.54 cm apart providing a 1.27 cm spatial resolution are crossed. Data is collected and analysed using TruScan Photo Beam Activity system (Coulbourn Instruments, Philadelphia, USA). Each rat is placed in the arena for 30 min.

Example 5

The effects of Test Compounds on performance in different memory tasks in vivo are investigated in transgenic amyloidogenic Alzheimer's mouse models according to the following protocols.

Alzheimer's Mouse Lines

Two transgenic Alzheimer's mouse colonies are used in the experiments—(i) 5×FAD that expresses a transgene with 3 mutations in the human amyloid precursor protein (APP), 2 mutations in presenilin 1 (PS1) (Oakely et al, 2006) and (ii) APPswe/PS1ΔE9 which expresses the Swedish mutations in APP and PS1 carrying the exon 9-deleted variant (Jankowsky et al, 2004). The rationale for choosing these models is that the 5×FAD mouse has an aggressive, early onset form of the disease that reflects familial human AD whereas the APPswe/PS1ΔE9 mouse model demonstrates a progressive, later onset cognitive decline and Aβ pathology reflective of sporadic human AD cases.

Figure 2:
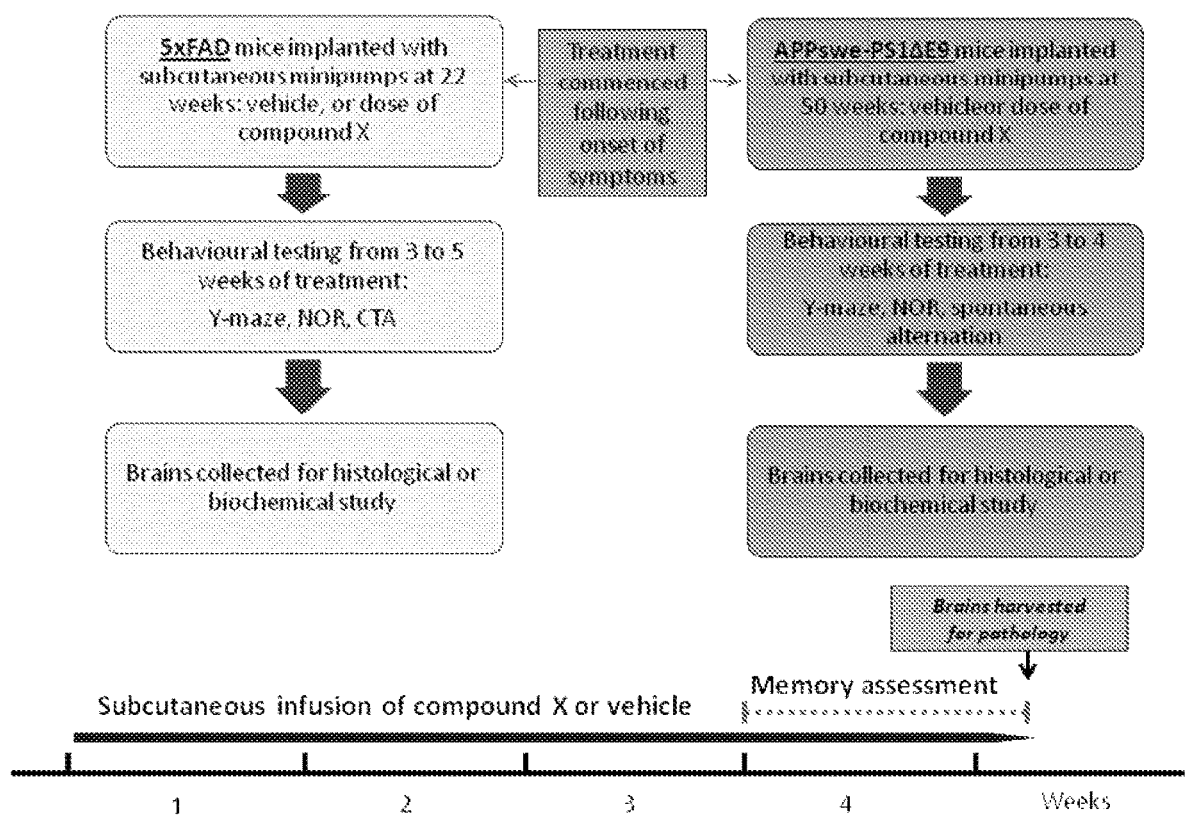
FIG. 2 schematically depicts the treatment regime for assessing activity of Test Compounds in AD mouse models.

The treatment regime is as set out in FIG. 2.

Y-Maze (Albiston et al, 2010)

The two-trial Y-maze is a test of hippocampus-dependent spatial memory, with no requirement for aversive stimuli or reward. The Y-shaped grey Perspex maze contains arms measuring 30×9.5×15.5 cm, each of which can be isolated with a sliding door. The maze is lined with bedding from the animal's home cage to enhance contrast for automated tracking and reduce cues from odour trails. Extra-maze cues are placed at the end of each arm (20-30 cm from the maze) as well as on the walls around the room (1-2 m from the maze): it has been demonstrated that extra-, and not intra-maze cues are required for performance of this task. Trials are recorded and analysed using Ethovision™ XT software (Noldus, Wageningen, The Netherlands). Mice are placed in the maze at the end of the start arm facing the end wall. In the first of two trials, one arm of the maze is randomly blocked off. Mice are allowed to explore this reduced maze for 10 minutes, after which time they are returned to their home cage. In the test trial, both arms are opened; the mouse is placed in the start arm and allowed to explore the maze for 5 minutes. The apparatus is cleaned with 70% alcohol, and bedding changed between animals.

The arm preferences are analysed using two related methods. Initially, the novel arm preference during the first minute of Trial 2 is calculated as Preference=N/(N+F)×100, where N is either time or number of entries in the novel arm, and F refers to the familiar arm. This two-arm analysis is devised to eliminate bias from time spent in the start arm, which is likely to be higher in anxious or hypoactive animals. The preference score for each group is analysed by a one-sample t-test to establish performance above chance levels, where chance is set at 50%.

Example 6

The effects of Test Compounds on amyloid pathology and neuroinflammatory markers are investigated in transgenic amyloidogenic Alzheimer's mouse models according to the following protocol.

Amyloid Plaque Staining

Coverage of thioflavin S, a fluorescent dye that binds to β-pleated fibrils such as amyloid, is often employed to measure plaque density in transgenic mouse brain (Bussière et al., 2004). Measurement of thioflavin S fluorescence in brain sections is also commonly used to determine disease modifying effects of drug treatment in mice Maezawa et al, 2008; Kalinin et al., 2011). At the conclusion of the behavioral experiments, the mice are transcardially perfused with phosphate-buffered saline (PBS) following by 4% paraformaldehyde, the brains extracted, cryoprotected in 20% sucrose and snap frozen in isopentane on dry ice at −40° C. Twenty micron coronal sections are cut on a cryostat, incubated for 10 min with 0.1% (w/v) S-thioflavin (SigmaAldrich) dissolved in distilled water, rinsed with 70% ethanol and PBS and the fluorescent images are captured on a BX51 fluorescent microscope. Where possible, mosaic images of complete sections are compiled using Neurolucida (version 7.53.3, MBF BioScience, Williston, USA) using the automated x-y stage on the microscope/Regions selected for plaque density analysis are the dorsal subiculum and retrosplenial cortex for the 5xFAD mice, and the hippocampus and entorhinal cortex for the APP/PS1 mice.

Neuroinflammatory Marker Staining in AD Brain—Determination of Microglia Coverage Twenty-micron coronal sections are cut in a cryostat and mounted onto gelatin-coated glass slides. Non-specific binding is blocked by room temperature incubation in 10% normal donkey serum (Invitrogen, Sydney, Australia) in PBSX for two hours. For polyclonal antibodies, sections are then incubated with primary antibody (see conditions in Table 6-1 for the individual antibodies) in the presence of 3% serum in PBSX overnight at 4° C., washed and then incubated with an AlexaFluor®—conjugated secondary antibody (Invitrogen), diluted 1:500, for 2 hours at room temperature. Mouse monoclonal antibodies are applied using the Vector® M.O.M™ kit as directed in the manufacturer's instructions (VectorLabs, Burlingame, USA).

TABLE 6-1

| Antibody, clone, host, source | Target | Protocol | Secondary Antibody | Protocol |
|---|---|---|---|---|
| GFAP, 2.2B10, rat, Invitrogen | Astrocytes | 1:1000, 1 hour RT$^a$ | AlexaFluor 568 or 594 donkey anti-rat | 1:500, 2 hours RT |
| CD11b, M1/70.15, rat, AbD Serotec | Microglia | 1:1000, 16 hours 4° C. | AlexaFluor 568 or 594 donkey anti-rat | 1:500, 2 hours RT |
| Aβ, 6E10, mouse, Covance | Aβ 1-16 | 1:1000, 30 min RT | Cy5 donkey anti-mouse (Jackson ImmunoResearch) | 1:500, 30 min RT |

Images are obtained from sections immunostained with GFAP and CD11b antibodies, converted to 8-bit grey scale, background subtracted and the threshold set manually in Image J. The measurement function is again used to calculate the percentage of each section covered by immunoreactivity. CD11b immunostaining coverage is measured in the areas with abundant plaque coverage, namely the subiculum and retrosplenial cortex in the 5xFAD mice and the hippocampus and entorhinal cortex in the APPswe/PS1ΔE9 mice.

Example 7

The effects of Test Compounds on pro- and anti-inflammatory cytokines are investigated in mixed astrocytes-neuronal cultures treated with the inflammatory mediator, lipopolysaccharise (LPS), according to the following protocol.

Primary mixed neurons and astrocytes are cultured from cortices of embryonic day 15 to 18 rats. Cortices are dissected from the brain and placed in cold Earle's Balanced Salt Solution (EBSS, Gibco). The brain tissue is then washed with EBSS and treated with 0.12% Trypsin for 20 min at 37° C. Following trypsin digestion, the tissue is resuspended in growth media DMEM/F12 supplemented with 20% horse serum, 100 units/ml Penicillin/streptomycin, 2 mM Sodium Pyruvate, N2 Supplement, 25 mM HEPES, 0.02 M glucose (Invitrogen). The cell suspension $10^6$ cells per well is plated at in 6-well plates coated with poly-D-lysine. The media of the mixed cultures is changed every three days. The cells on day 11 in vitro are pre-treated with Test Compound at 10 uM and 100 uM in 0.2% DMSO. Same IRAP inhibitor treatment is repeated on day 14 in vitro. Following drug treatment, cells at day 15 in vitro are incubated with LPS from *Salomonella typhimurium,* 5 ug/ml, 1 ug/ml and 0.2 ug/ml, Sigma Aldrich) to induce pro-inflammatory cytokines. Cells are collected at 24 h for cytokine determination by quantitative RT-PCR.

The cells are washed three times with PBS (4° C.). RNA is isolated with the TRIZOL reagent (Invitrogen). cDNA was synthetized using High Capacity cDNA Reverse Transcription Kits (Applied Biosystems). Quantitative RT-PCR is performed in three duplicates of each sample using TaqMan primer probes (Applied Biosystems) on an eppendorf thermocycler using assays-on-demand and chemistries as recommended by the manufacturer (Applied Biosystems). The PCR signal of the target transcript in the treatment groups is related to that of the control by relative quantification. For each sample, GAPDH CT values are subtracted from the gene of interest CT values to derive a $\Delta C_T$ value. The $2^{-\Delta\Delta C_T}$ method is used to analyse the relative changes in gene expression. The housekeeping gene GAPDH rRNA is used as internal control to normalize the PCR for the amount of RNA added to the reverse transcription reactions and the target gene expression is normalised to the control. TaqMan assays have the following identification numbers: GAPDH: Rn01775763_g1; TNF alpha: Rn00562055_m1.

BIBLIOGRAPHY

Albiston et al, J Biol Chem 276(52):48623-48626, 2001.
Albiston et al, Behav Brain Res 154:239-243, 2004.
Albiston et al, Neurobiol Learn Mem 93(1):19-30, 2010
Bevins et al., Nat Protoc 1(3): 1306-11, 2006.
Bussiere et al Am J Pathol. 165(3):987-95, 2004.
Fernando et al, Eur J Neurosci 28:588-598, 2008.
Greferath et al., Neuroscience 100: 363-373, 2000.
Janelsins et al, J Neuroinflammation 2:23, 2005.
Jankowsky et al, Hum Mol Gen 13(2):159-170, 2004.
Kalinin et al Neurobiol Aging. epub Jun. 24, 2011.
Karran et al, Nat Rev Drug Discov. 10(9):698-712, 2011.
Keller et al., J. Biol Chem 270: 23612-23618, 1995.
Lee et al., Neuroscience 124: 341-349, 2004.
Lew et al, J. Neurochem 86(2): 344-350, 2003.
McNay et al., Proc Natl Acad Sci USA, 97(6): 2881-5, 2000.
Maezawa et al, J. Neurochem 104(2):457-68, 200
Matsumoto et al, Eur J Biochem 268(11):3259-3266, 2001.
Oakley et al, J Neurosci 26(40): 10129-40, 2006.
Rogi et al, J Biol Chem 271(1):56-61, 1996.
Selkoe, Cold Spring Harb Perspect Biol. 3(7). pii: a004457, 2011.

The invention claimed is:

1. A compound of Formula (I),

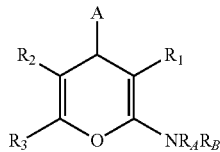

(I)

wherein

A is selected from phenyl, pyridinyl, pyrazinyl, pyrimidinyl and pyridazinyl, which is substituted by at least one of CO$_2$H or a carboxylic acid isostere, wherein the carboxylic isostere is selected from —SO$_3$H, —SO$_2$NH$_2$, —SO$_2$NHR, —PO$_2$H$_2$, —PO$_2$HR, —SH, —NHCOH, —CONH$_2$, —CONHR, —CONH(O)H, —CONH(O)R, —CONHNHSO$_2$H, —CONHNHSO$_2$R, —COHNSO$_2$—H, —COHNSO$_2$R and —CONH—CN, where R is selected from alkyl, phenyl and benzyl; and carbocyclic and heterocyclic groups selected from:

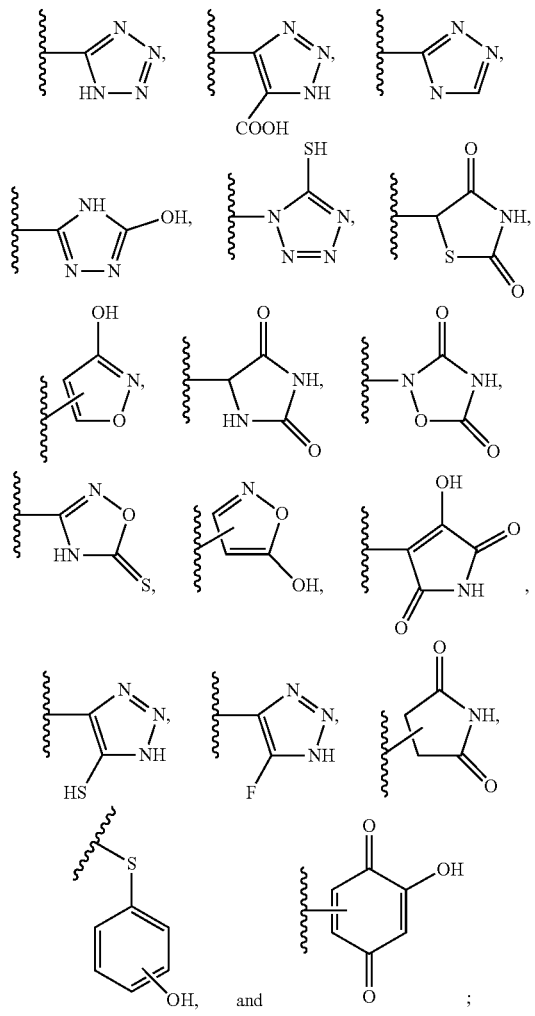

and wherein said phenyl, pyridinyl, pyrazinyl, pyrimidinyl and pyridazinyl may be further optionally substituted by one or more substituents;

R$_A$ and R$_B$ are independently selected from hydrogen, alkyl and acyl, and wherein at least one of R$_A$ and R$_B$ is hydrogen;

R$_1$ is selected from CN and CO$_2$R$_C$;

R$_2$ is selected from CO$_2$R$_C$ and acyl;

R$_3$ is selected from alkyl, alkenyl, alkynyl, aryl, arylalkyl, heteroaryl, heteroarylalkyl, carbocyclyl, carbocyclylalkyl, each of which maybe optionally substituted;

R$_C$ is selected from alkyl, alkenyl, alkynyl, aryl, arylalkyl, heteroaryl, heteroarylalkyl, carbocyclyl, carbocyclylalkyl, each of which may be optionally substituted, or a pharmaceutically acceptable salt or solvate thereof.

2. The compound according to claim 1, wherein one of R$_A$ and R$_B$ is hydrogen and the other is alkyl or acyl.

3. The compound according to claim 1, wherein R$_A$ and R$_B$ are independently selected from alkyl and acyl.

4. The compound according to claim 1, wherein R$_2$ and R$_3$ together form a 5-6-membered saturated keto-carbocyclic ring:

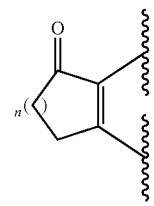

wherein n is 1 or 2;

and which ring may be optionally substituted one or more times by C$_{1-6}$alkyl; or R$_2$ and R$_3$ together form a 5-membered lactone ring (a) or a 6-membered lactone ring (b)

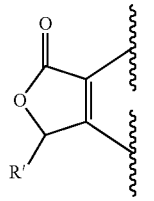

(a)

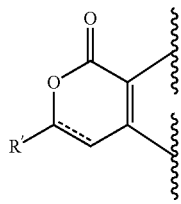

(b)

wherein ---- is an optional double bond and R' is alkyl.

5. The compound according to claim 1, wherein A is selected from phenyl and pyridinyl.

6. The compound according to claim 1, wherein A is phenyl.

7. The compound according to claim 1, wherein R$_A$ and R$_B$ are both hydrogen.

8. The compound according to claim 1, wherein $R_1$ is selected from CN, $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered heteroaryl, $CO_2(CH_2)_{1-6}$-5-6-membered heteroaryl, $CO_2C_{3-6}$cycloalkyl, and $CO_2(CH_2)_{1-6}C_{3-6}$cycloalkyl.

9. The compound according to claim 1, wherein $R_2$ is selected from $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered $CO_2$heteroaryl, $CO_2(CH_2)_{1-6}$-5-6-membered heteroaryl, $CO_2C_{3-6}$cycloalkyl, $CO_2(CH_2)_{1-6}C_{3-6}$cycloalkyl, $C(O)C_{1-6}$alkyl, $C(O)C_{1-6}$alkenyl, $C(O)C_{1-6}$alkynyl, $C(O)$phenyl, $C(O)(CH_2)_{1-6}$phenyl, $C(O)$5-6-membered heteroaryl, $C(O)(CH_2)_{1-6}$-5-6-membered heteroaryl, $C(O)C_{3-6}$cycloalkyl, or $C(O)(CH_2)_{1-6}C_{3-6}$cycloalkyl, each of which may be optionally substituted.

10. The compound according to claim 1, wherein $R_3$ is alkyl.

11. The compound according to claim 1, wherein $R_2$ is selected from $CO_2R_C$ and acyl; and $R_3$ is selected from alkyl, alkenyl, alkynyl, aryl, arylalkyl, heteroaryl, heteroarylalkyl, carbocyclyl, carbocyclylalkyl, each of which may be optionally substituted.

12. The compound according to claim 1, wherein $R_1$ is selected from CN, $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered heteroaryl, $CO_2(CH_2)_{1-6}$-5-6-membered heteroaryl, $CO_2C_{3-6}$cycloalkyl, and $CO_2(CH_2)_{1-6}C_{3-6}$cycloalkyl;

$R_2$ is selected from $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered $CO_2$heteroaryl, $CO_2(CH_2)_{1-6}$-5-6-membered heteroaryl, $CO_2C_{3-6}$cycloalkyl, $CO_2(CH_2)_{1-6}C_{3-6}$cycloalkyl, $C(O)C_{1-6}$alkyl, $C(O)C_{1-6}$alkenyl, $C(O)C_{1-6}$alkynyl, $C(O)$phenyl, $C(O)(CH_2)_{1-6}$phenyl, $C(O)$5-6-membered heteroaryl, $C(O)(CH_2)_{1-6}$-5-6-membered heteroaryl, $C(O)C_{3-6}$cycloalkyl, or $C(O)(CH_2)_{1-6}C_{3-6}$cycloalkyl, each of which may be optionally substituted; and $R_3$ is alkyl.

13. A compound according to claim 1, wherein the compound is selected from the group consisting of:

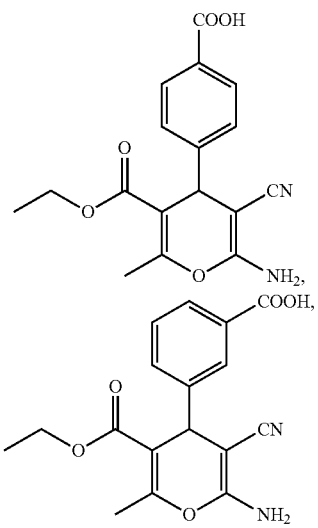

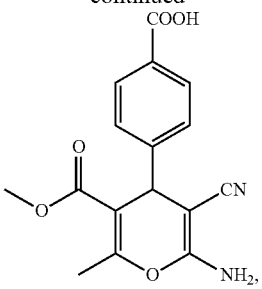

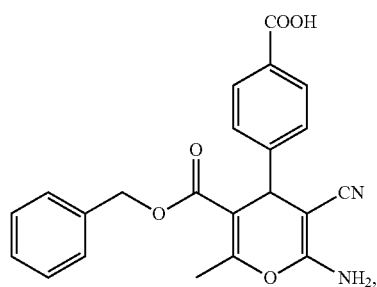

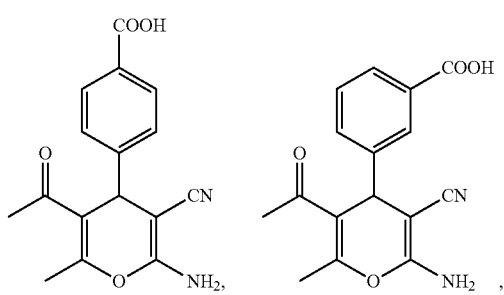

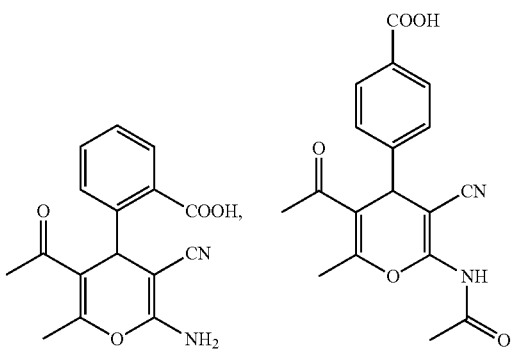

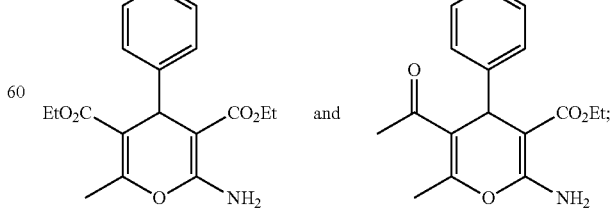

or a pharmaceutically acceptable salt or solvate thereof.

14. A composition comprising a compound of Formula (I),

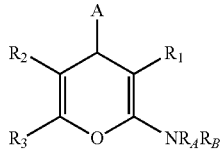

wherein
A is selected from phenyl, pyridinyl, pyrazinyl, pyrimidinyl and pyridazinyl, which is substituted by at least one of $CO_2H$ or a carboxylic acid isostere, wherein the carboxylic isostere is selected from —$SO_3H$, —$SO_2NH_2$, —$SO_2NHR$, —$PO_2H_2$, —$PO_2HR$, —SH, —NHCOH, —$CONH_2$, —CONHR, —CONH(O)H, —CONH(O)R, —$CONHNHSO_2H$, —$CONHNHSO_2R$, —$COHNSO_2$—H, —$COHNSO_2R$ and —CONH—CN, where R is selected from alkyl, phenyl and benzyl; and carbocyclic and heterocyclic groups selected from:

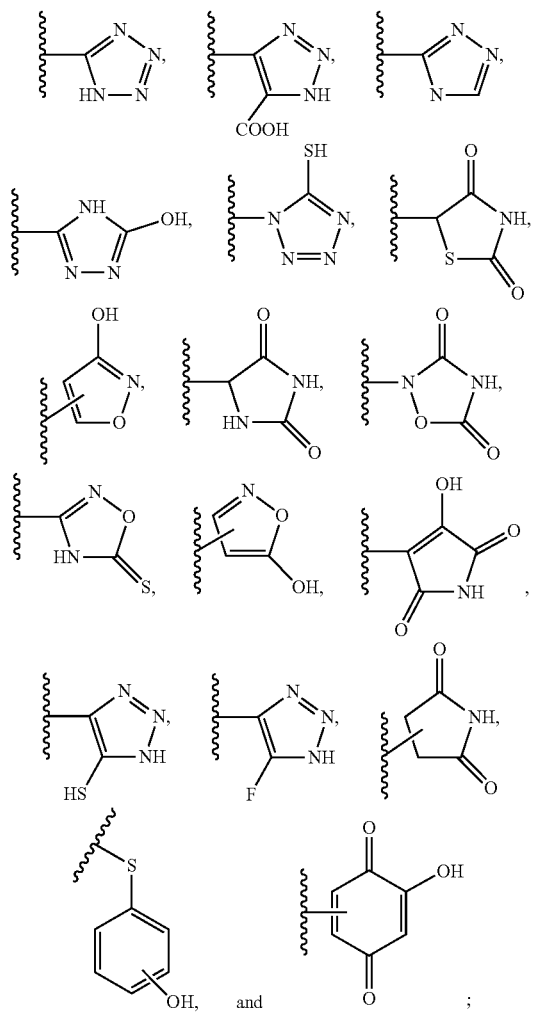

and wherein said phenyl, pyridinyl, pyrazinyl, pyrimidinyl and pyridazinyl may be further optionally substituted by one or more substituents;

$R_A$ and $R_B$ are independently selected from hydrogen, alkyl and acyl, and wherein at least one of $R_A$ and $R_B$ is hydrogen;

$R_1$ is selected from CN and $CO_2R_C$;

$R_2$ is selected from $CO_2R_C$ and acyl;

$R_3$ is selected from alkyl, alkenyl, alkynyl, aryl, arylalkyl, heteroaryl, heteroarylalkyl, carbocyclyl, carbocyclylalkyl, each of which maybe optionally substituted;

$R_C$ is selected from alkyl, alkenyl, alkynyl, aryl, arylalkyl, heteroaryl, heteroarylalkyl, carbocyclyl, carbocyclylalkyl, each of which may be optionally substituted, or a pharmaceutically acceptable salt or solvate thereof, and a pharmaceutically acceptable additive.

15. The composition according to claim 14, wherein A is selected from phenyl and pyridinyl.

16. The composition according to claim 14, wherein A is phenyl.

17. The composition according to claim 14, wherein $R_A$ and $R_B$ are both hydrogen.

18. The composition according to claim 14, wherein $R_1$ is selected from CN, $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered heteroaryl, $CO_2(CH_2)_{1-6}$-5-6-membered heteroaryl, $CO_2C_{3-6}$cycloalkyl, and $CO_2(CH_2)_{1-6}C_{3-6}$cycloalkyl.

19. The composition according to claim 14, wherein $R_2$ is selected from $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered $CO_2$heteroaryl, $CO_2(CH_2)_{1-6}$-5-6-membered heteroaryl, $CO_2C_{3-6}$cycloalkyl, $CO_2(CH_2)_{1-6}C_{3-6}$cycloalkyl, $C(O)C_{1-6}$alkyl, $C(O)C_{1-6}$alkenyl, $C(O)C_{1-6}$alkynyl, C(O)phenyl, $C(O)(CH_2)_{1-6}$phenyl, C(O)5-6-membered heteroaryl, $C(O)(CH_2)_{1-6}$-5-6-membered heteroaryl, $C(O)C_{3-6}$cycloalkyl, or $C(O)(CH_2)_{1-6}C_{3-6}$cycloalkyl, each of which may be optionally substituted.

20. The composition according to claim 14, wherein $R_3$ is alkyl.

21. A method of treating or preventing memory loss or impairment or improving cognition and/or memory in a subject in need thereof comprising administering to said subject a compound of Formula (I), or a pharmaceutically acceptable salt, solvate or prodrug thereof, as defined in claim 1.

22. A method of treating or preventing Alzheimer's Disease in a subject in need thereof comprising administering to said subject a compound of Formula (I), or a pharmaceutically acceptable salt, solvate or prodrug thereof, as defined in claim 1.

23. The composition according to claim 14 wherein $R_2$ is selected from $CO_2R_C$ and acyl; and
$R_3$ is selected from alkyl, alkenyl, alkynyl, aryl, arylalkyl, heteroaryl, heteroarylalkyl, carbocyclyl, carbocyclylalkyl, each of which may be optionally substituted.

24. The composition according to claim 14, wherein $R_1$ is selected from CN, $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered heteroaryl, $CO_2(CH_2)_{1-6}$-5-6-membered heteroaryl, $CO_2C_{3-6}$cycloalkyl, and $CO_2(CH_2)_{1-6}C_{3-6}$cycloalkyl;
$R_2$ is selected from $CO_2C_{1-6}$alkyl, $CO_2C_{1-6}$alkenyl, $CO_2C_{1-6}$alkynyl, $CO_2$phenyl, $CO_2(CH_2)_{1-6}$phenyl, $CO_2$5-6-membered $CO_2$heteroaryl, $CO_2(CH_2)_{1-6}$-5-6-membered heteroaryl, $CO_2C_{3-6}$cycloalkyl, $CO_2(CH_2)_{1-6}C_{3-6}$cycloalkyl, $C(O)C_{1-6}$alkyl, $C(O)C_{1-6}$alkenyl, $C(O)C_{1-6}$alkynyl, C(O)phenyl, $C(O)(CH_2)_{1-6}$phenyl, C(O)5-6-membered heteroaryl, $C(O)(CH_2)_{1-6}$-5-6- membered heteroaryl, C(O)C$_{3-6}$cycloalkyl, or C(O)(CH$_2$)$_{1-6}$C$_{3-6}$cycloalkyl, each of which may be optionally substituted; and
R$_3$ is alkyl.
25. A composition according to claim 14, wherein the compound is selected from the group consisting of:
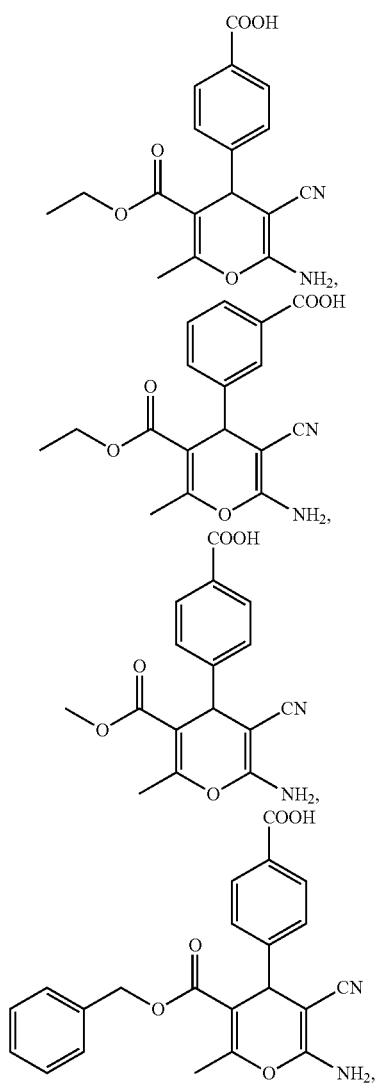
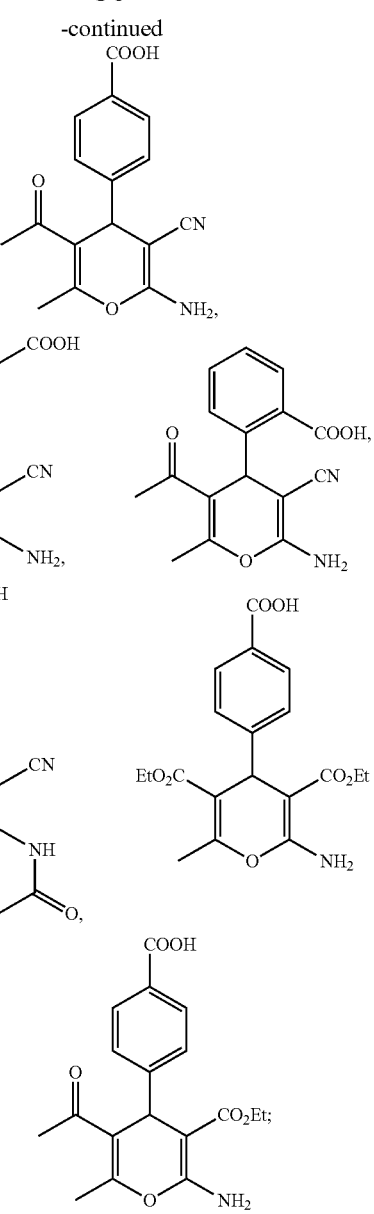
or a pharmaceutically acceptable salt or solvate thereof.
* * * * *